US009538952B2

(12) United States Patent
LaFarge

(10) Patent No.: US 9,538,952 B2
(45) Date of Patent: Jan. 10, 2017

(54) CONTROLLER FOR MEASURING PROSTATE VOLUME

(71) Applicant: MedicaMetrix, Inc., Wayland, MA (US)

(72) Inventor: Christopher LaFarge, Wayland, MA (US)

(73) Assignee: MedicaMetrix, Inc., Wayland, MA (US)

( * ) Notice: Subject to any disclaimer, the term of this patent is extended or adjusted under 35 U.S.C. 154(b) by 949 days.

(21) Appl. No.: 13/663,890

(22) Filed: Oct. 30, 2012

(65) Prior Publication Data

US 2014/0121536 A1 May 1, 2014

(51) Int. Cl.
*A61B 6/00* (2006.01)
*A61B 5/00* (2006.01)

(52) U.S. Cl.
CPC .......... *A61B 5/4381* (2013.01); *A61B 5/6806* (2013.01); *A61B 5/6826* (2013.01); *A61B 2562/228* (2013.01)

(58) Field of Classification Search
CPC ..... A61B 5/076; A61B 5/1076; A61B 5/1079; A61B 5/4381; A61B 5/6806; A61B 5/6826
See application file for complete search history.

(56) References Cited

U.S. PATENT DOCUMENTS

| 3,904,269 | A | 9/1975 | Lebduska et al. |
| 5,059,477 | A | 10/1991 | Henriksen |
| 5,097,252 | A | 3/1992 | Harvill et al. |
| 5,196,247 | A | 3/1993 | Wu et al. |
| 5,265,181 | A | 11/1993 | Chang |
| 5,279,309 | A * | 1/1994 | Taylor ................ A61B 19/5244 600/595 |

(Continued)

FOREIGN PATENT DOCUMENTS

| WO | 00/13591 A1 | 3/2000 |
| WO | 2005/021049 A2 | 3/2005 |

(Continued)

OTHER PUBLICATIONS

Eri et al (Accuracy and repeatability of prostate volume measurements by transrectal ultrasound, Prostate Cancer and Prostatic Diseases (2002) 5, 273-278.*

(Continued)

*Primary Examiner* — James Kish
*Assistant Examiner* — Saurel J Selkin
(74) *Attorney, Agent, or Firm* — Nutter McClennen & Fish LLP

(57) ABSTRACT

Systems and methods are provided herein that generally involve measuring a prostate or other object. In some embodiments, a membrane can be sealed over a digit extension to form a closed volume. The closed volume can be inflated via an inflation tube, and a reference pattern can be disposed within the closed volume along with a measurement assembly. In use, a user can put on the glove, position the membrane in proximity to a rectal wall overlying a prostate, and inflate the membrane. As the user slides their finger across the rectal wall, optical fibers in the measurement assembly can move relative to a reference pattern, and a controller can sense light reflected through the fibers from the reference pattern. The controller can calculate or estimate various attributes of the prostate based on the reflected light, such as the palpable surface width or volume.

14 Claims, 20 Drawing Sheets

(56) References Cited

U.S. PATENT DOCUMENTS

| | | | |
|---|---|---|---|
| 5,423,332 | A | 6/1995 | Zirps et al. |
| 5,582,620 | A | 12/1996 | Hirsch |
| 5,867,831 | A | 2/1999 | Husain |
| 5,922,018 | A | 7/1999 | Sarvazyan |
| 5,965,276 | A | 10/1999 | Shlenker et al. |
| 6,142,959 | A | 11/2000 | Sarvazyan et al. |
| 6,360,116 | B1 | 3/2002 | Jackson, Jr. et al. |
| 6,709,142 | B2 | 3/2004 | Gyori |
| 6,743,165 | B2 | 6/2004 | Mosel et al. |
| 6,829,421 | B2 | 12/2004 | Forbes et al. |
| 7,254,842 | B2 | 8/2007 | Becerra et al. |
| 7,309,319 | B2 | 12/2007 | Kellett et al. |
| 7,354,202 | B1 | 4/2008 | Luger |
| 7,359,742 | B2 | 4/2008 | Maser et al. |
| 7,582,056 | B2 | 9/2009 | Noguchi et al. |
| 7,662,113 | B2 | 2/2010 | Pearl et al. |
| 8,092,372 | B2 | 1/2012 | Machida |
| 8,104,097 | B2 | 1/2012 | Hamann |
| 8,694,079 | B1 | 4/2014 | LaFarge |
| 2003/0210259 | A1 | 11/2003 | Liu et al. |
| 2004/0213445 | A1 | 10/2004 | Lee et al. |
| 2006/0026737 | A1 | 2/2006 | Chen |
| 2006/0052663 | A1 | 3/2006 | Koitabashi |
| 2006/0069721 | A1 | 3/2006 | Dowling |
| 2006/0106294 | A1 | 5/2006 | Maser et al. |
| 2006/0116552 | A1 | 6/2006 | Noguchi et al. |
| 2006/0122538 | A1* | 6/2006 | Kellett ............... A61B 5/1076 600/587 |
| 2006/0129070 | A1 | 6/2006 | Pearl et al. |
| 2007/0244363 | A1 | 10/2007 | Sano et al. |
| 2007/0293792 | A1 | 12/2007 | Sliwa et al. |
| 2008/0200926 | A1* | 8/2008 | Verard ............... A61B 19/44 606/130 |
| 2008/0306387 | A1 | 12/2008 | Schutz et al. |
| 2009/0023996 | A1 | 1/2009 | Fujikura |
| 2009/0068443 | A1 | 3/2009 | Curtet et al. |
| 2009/0069721 | A1 | 3/2009 | Kellett et al. |
| 2009/0209813 | A1 | 8/2009 | Lubowski et al. |
| 2010/0256461 | A1 | 10/2010 | Mohamedali et al. |
| 2010/0262020 | A1 | 10/2010 | Backman et al. |
| 2010/0305400 | A1 | 12/2010 | Onoda et al. |
| 2011/0172563 | A1 | 7/2011 | Kellett et al. |
| 2011/0302694 | A1 | 12/2011 | Wang et al. |
| 2013/0023770 | A1 | 1/2013 | Courtney et al. |
| 2014/0121529 | A1 | 5/2014 | LaFarge |
| 2014/0121533 | A1 | 5/2014 | LaFarge |
| 2014/0121534 | A1 | 5/2014 | LaFarge |
| 2014/0121535 | A1 | 5/2014 | LaFarge |
| 2014/0121562 | A1 | 5/2014 | LaFarge |
| 2014/0121563 | A1 | 5/2014 | LaFarge |

FOREIGN PATENT DOCUMENTS

| | | |
|---|---|---|
| WO | 2005/051191 A1 | 6/2005 |
| WO | 2009/067573 A3 | 9/2009 |

OTHER PUBLICATIONS

[No Author Listed] Industrial Fiber Optics, SK-20; 0.5mm Optical Fiber High Performance Plastic Optical Fiber, Jul. 10, 2010. https://web.archive.org/web/20100710185724/http://i-fiberoptics.com/fiber-detail.php?id=122 (1 page).

International Search Report and Written Opinion for Application No. PCT/US2013/063986 mailed Apr. 11, 2014 (19 Pages).

U.S. Appl. No. 13/663,877, filed Oct. 30, 2012, Prostate Glove With Measurement Grid.

U.S. Appl. No. 13/663,879, filed Oct. 30, 2012, Grid for Measuring Prostate Volume.

U.S. Appl. No. 13/663,881, filed Oct. 30, 2012, Prostate Glove With Receiver Fibers.

U.S. Appl. No. 13/663,883, filed Oct. 30, 2012, Finger Clip for Prostate Glove.

U.S. Appl. No. 13/663,888, filed Oct. 30, 2012, Connector for Use With a Prostate Measurement System.

U.S. Appl. No. 13/663,875, filed Oct. 30, 2012, Double Membrane Prostate Glove.

[No Author Listed] Fiber Optics Light Glove. Designboom. Sep. 28, 2007, 1 page, Retrieved from <http://www.designboom.com/project/fiber-optics-light-glove/>.

Extended European Search Report for Application No. 13852114.1, issued May 11, 2016 (6 pages).

International Application No. PCT/US08/084112—International Search Report, Written Opinion, and IPRP.

International Application No. PCT/US04/039664—International Search Report, Written Opinion, and IPRP.

* cited by examiner

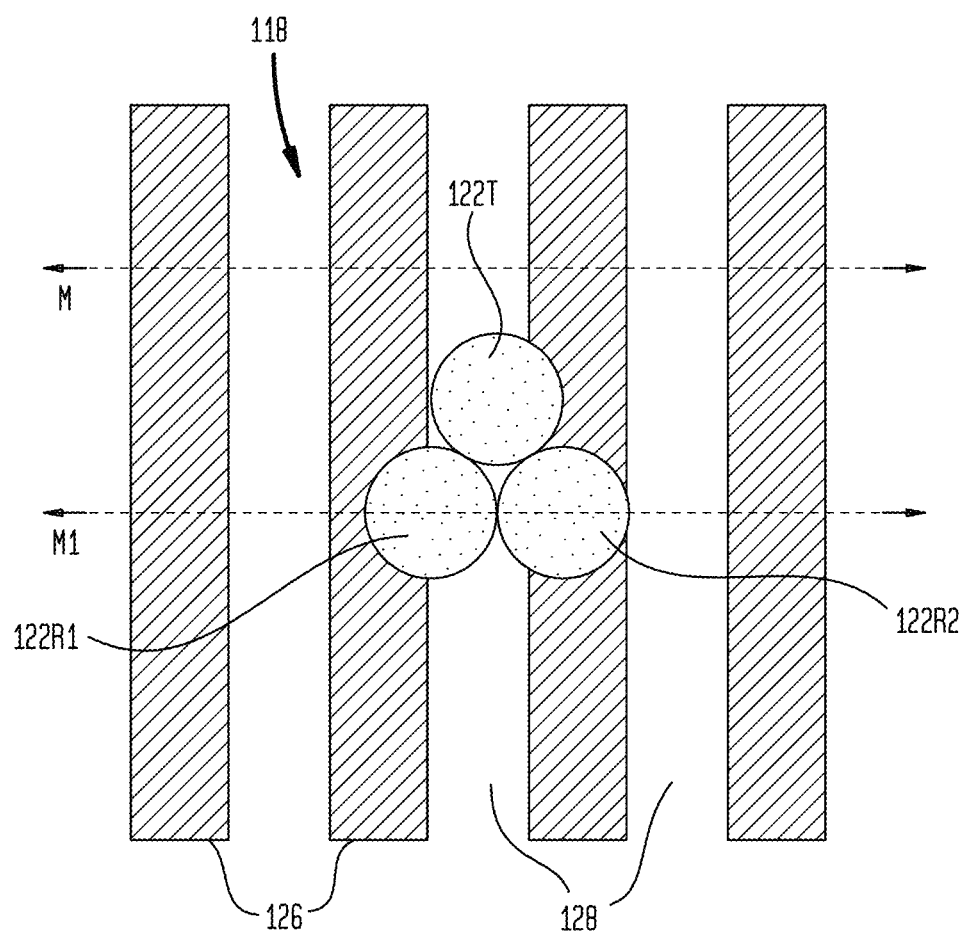

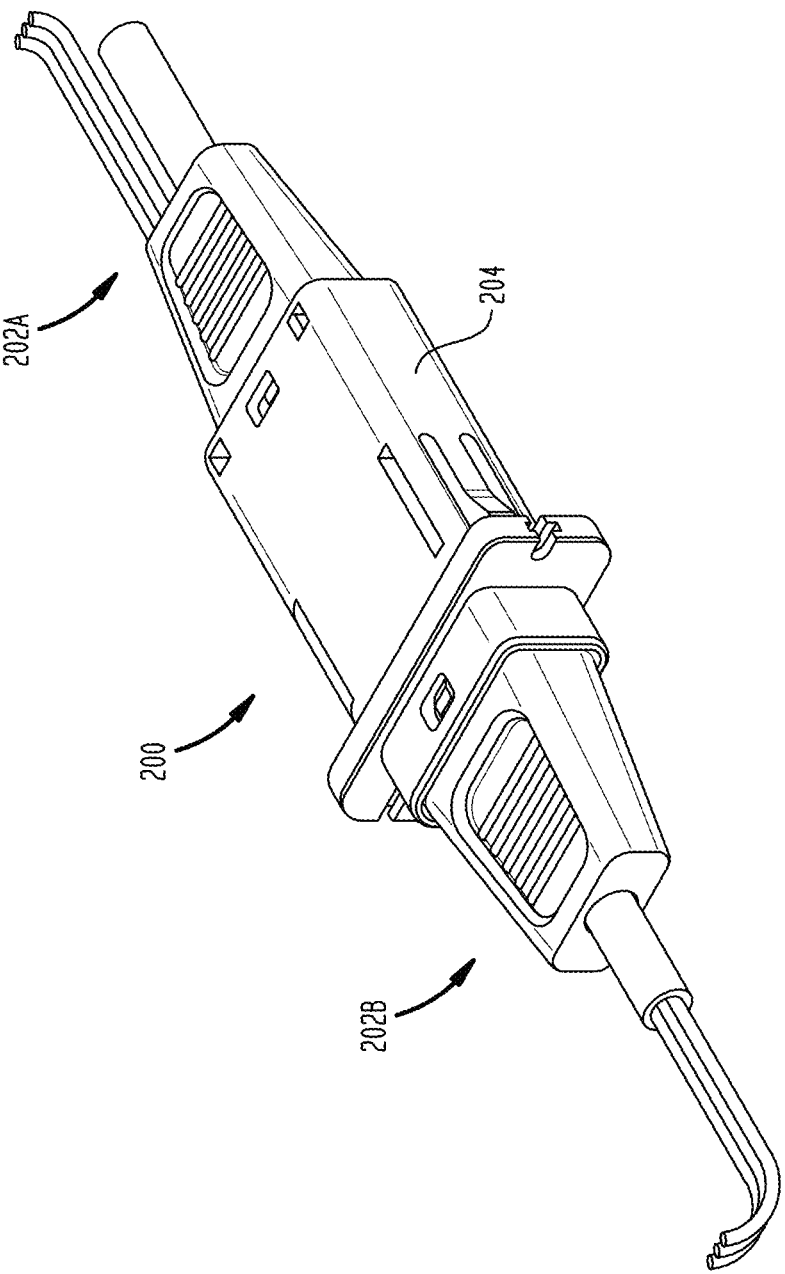

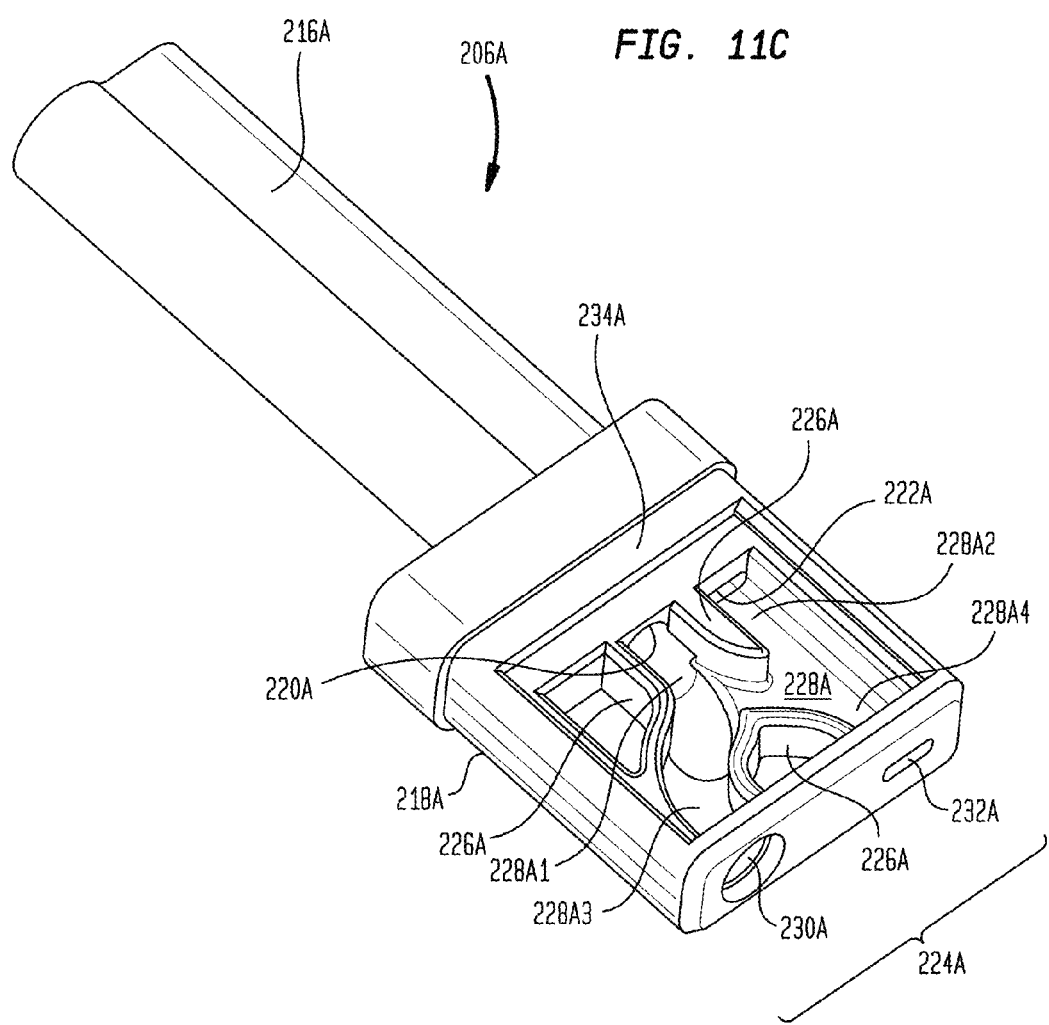

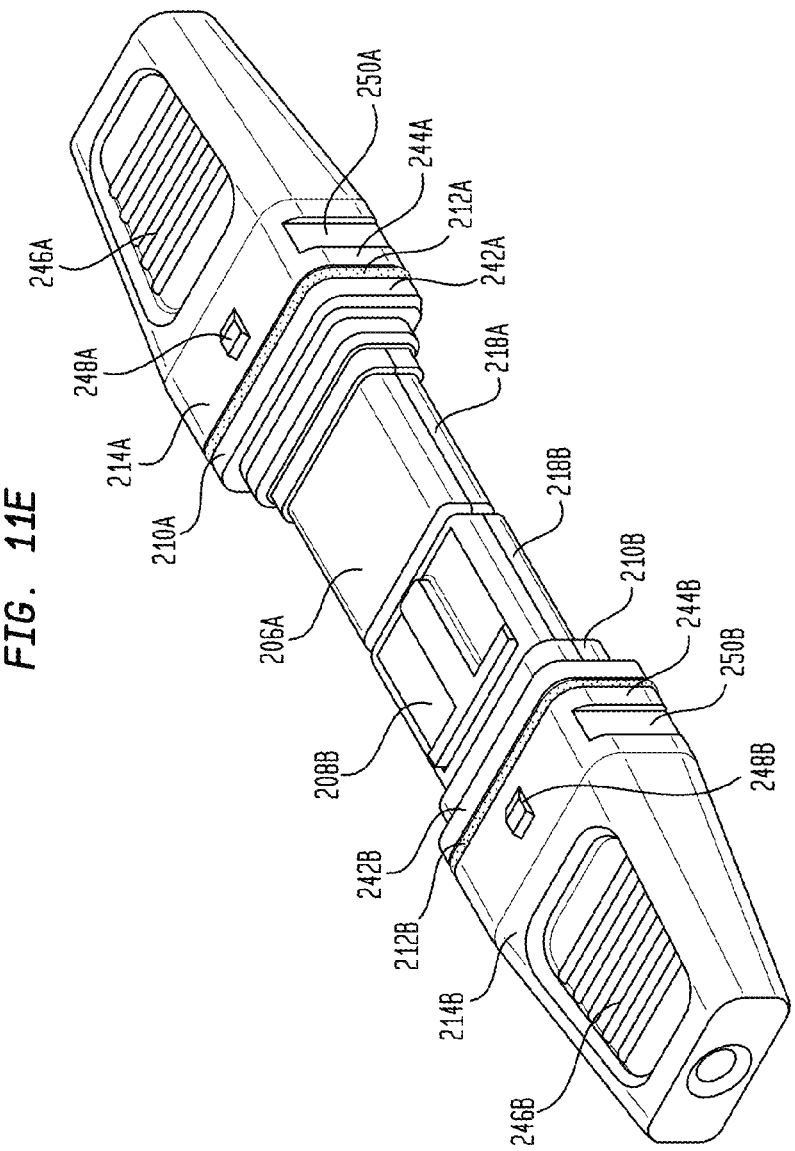

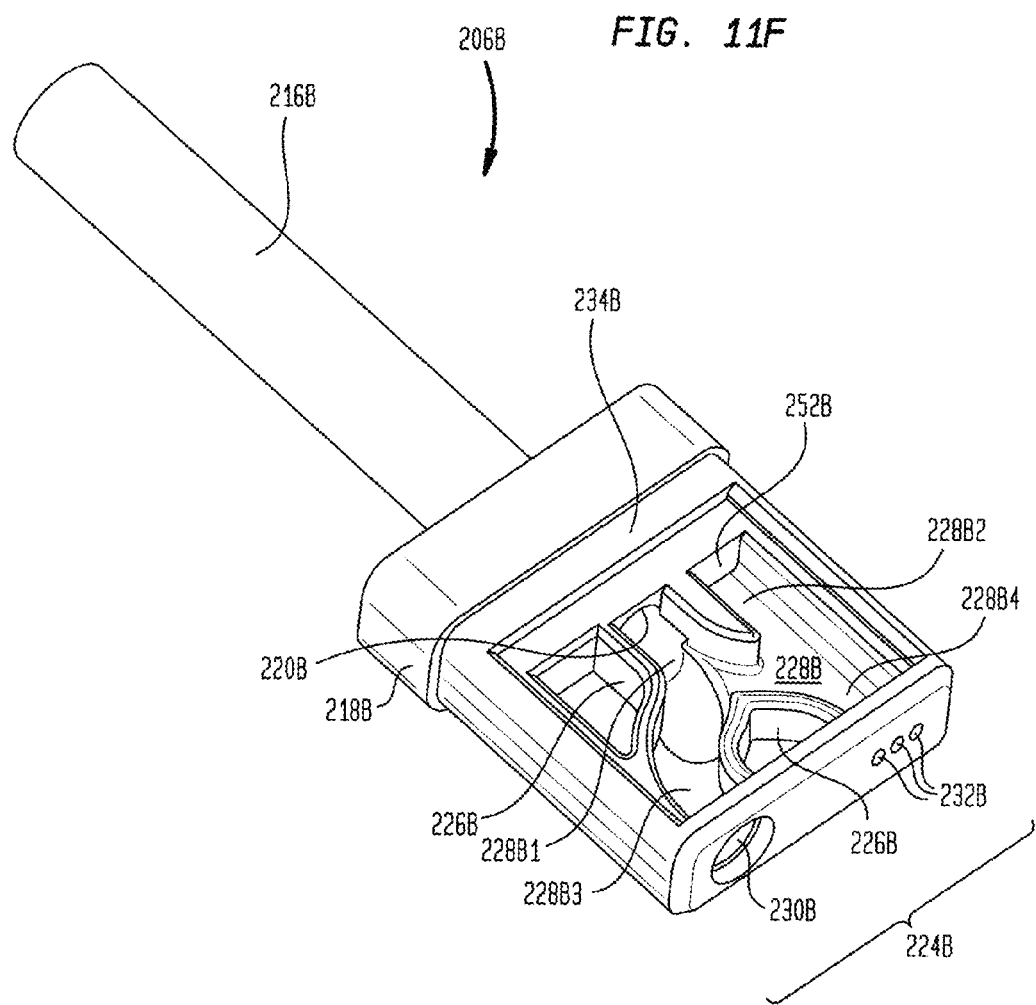

CONTROLLER FOR MEASURING PROSTATE VOLUME

FIELD

The present disclosure relates to systems and methods for measuring or evaluating an object. In some embodiments, systems and methods for measuring the prostate are provided.

BACKGROUND

Prostate problems are widespread in the male population, especially the older male population. In particular, benign prostatic hyperplasia (BPH) and prostate cancer are common in men over 50 years of age. Indeed, prostate cancer is the second most common cancer in men in the United States. Each year, there are more than 200,000 new cases and more than 30,000 deaths. However, if prostate cancer is detected early and treated effectively, the chance of survival improves significantly. Unfortunately, conventional methods for detecting prostate problems are wanting as many early stage cancers go undetected.

While ultrasound systems have been developed to diagnose prostate problems, such systems are very expensive. Most ultrasound imaging is performed by radiologists at an outside facility, or at the practitioner's office on a contract basis with a portable ultrasound unit. The technology and interpretation is difficult to master, requiring a time-consuming learning curve. Consequently, no routine examining system or technique exists which provides a high degree of accuracy in measuring prostate volume, nor is the required repeatability of results achieved.

Thus, the digital rectal examination continues to be the modality of choice for monitoring the prostate even though the process is very subjective. The standard exam is done by inserting a finger into the rectum and palpating or feeling the palpable surface of the prostate. The physical characteristics of the prostate size, contour, consistency, symmetry, and the presence or absence of nodularity, are assessed and recorded by attempting to translate the physician's subjective impressions into a written record. This method of data collection is inexact and makes comparisons from exam to exam very difficult.

Exemplary methods and devices for measuring the prostate are disclosed in U.S. Pat. No. 7,309,319, entitled "APPARATUS AND METHOD FOR MEASURING THE DIMENSIONS OF THE PALPABLE SURFACE OF THE PROSTATE," U.S. Publication No. 2009/0069721, entitled "APPARATUS AND METHOD FOR MEASURING THE DIMENSIONS OF THE PALPABLE SURFACE OF THE PROSTATE," and U.S. Publication No. 2011/0172563, entitled "APPARATUS AND METHOD FOR MEASURING THE DIMENSIONS OF THE PALPABLE SURFACE OF THE PROSTATE," the entire contents of each of which are incorporated herein by reference in their entirety.

SUMMARY

Systems and methods are provided herein that generally involve measuring a prostate or other object. In some embodiments, a reference pattern is positioned adjacent to the object to be measured and light reflected from the reference pattern is measured or interpreted to estimate various attributes of the object, such as its volume. For example, a membrane can be sealed over a glove to form a closed volume. The closed volume can be configured to be expanded via an inflation tube, and a reference pattern can be disposed within the closed volume along with one or more optical fibers. In use, a user can put on the glove, position the membrane in proximity to a rectal wall overlying a prostate, and inflate the membrane. As the user slides their finger across the rectal wall, the optical fibers move relative to the reference pattern and a controller senses light reflected through the fibers from the reference pattern. The controller can calculate or estimate various attributes of the prostate based on the reflected light, such as the palpable surface width or volume.

In one aspect, an examination device is provided that includes a glove configured to be removably disposed around a human hand, the glove having a digit extension configured to receive a human digit of a human hand disposed within the glove. The device can include a membrane disposed over at least a portion of the digit extension, the membrane and the digit extension forming a closed volume therebetween. The device can also include a reference pattern disposed within the closed volume, and at least one optical fiber extending into the closed volume and in optical communication with the reference pattern, the optical fiber being configured to move relative to the reference pattern.

An inflation tube can extend into the closed volume through which an inflation medium can be supplied to inflate the membrane relative to the digit extension. In one embodiment, the at least one fiber can extend through the inflation tube. In certain aspects, the membrane can be in the form of an elongate tubular body having a closed distal end and a proximal end that is sealed circumferentially around the digit extension. The membrane can be sealed to the digit extension, for example, using an adhesive. In other aspects, the optical fiber can be coupled to the digit extension and the reference pattern can be coupled to the membrane. In an exemplary embodiment, the at least one optical fiber can include a first transmitting fiber configured to direct light generated by an external light source onto the reference pattern, and a first receiver fiber configured to direct light reflected by the reference pattern to a first external optical detector. The at least one optical fiber can further include a second receiver fiber configured to direct light reflected by the reference pattern to a second external optical detector. The first transmitter fiber, the first receiver fiber, and the second receiver fiber can extend through an inflation tube configured to supply an inflation medium to the closed volume.

In another aspect, an examination device is provided that includes a glove configured to be removably disposed around a human hand, an inflatable membrane sealed around at least a portion of the glove to define a closed volume between the membrane and the glove, a reference pattern coupled to a surface of the membrane, and at least one optical fiber extending into the closed volume and coupled to the glove such that the at least one optical fiber is movable with the portion of the glove relative to the membrane, the at least one optical fiber being in optical communication with the reference pattern.

The at least one optical fiber can include a first transmitter fiber, a first receiver fiber, and a second receiver fiber. The device can include an inflation tube in fluid communication with the closed volume for delivering an inflation fluid into the closed volume to inflate the membrane relative to the glove. The at least one optical fiber can extend through the inflation tube.

In another aspect, a method of measuring a prostate is provided that includes positioning a digit extension of a glove in proximity to a rectal wall adjacent the prostate, the digit extension having at least one optical fiber coupled thereto and a membrane disposed therearound to form a closed volume. The method can also include inflating the closed volume relative to the digit extension such that the membrane contacts the rectal wall, and moving the at least one optical fiber across a reference pattern disposed within the closed volume from a first lateral margin of the prostate to a second lateral margin of the prostate, thereby generating information indicative of a distance traveled by the at least one optical fiber.

The method can include using at least one processor to correlate the information indicative of a distance traveled by the at least one optical fiber with a palpable surface width of the prostate. The method can include using at least one processor to correlate the palpable surface width of the prostate with a volume of the prostate. The at least one optical fiber can be coupled to the digit extension, the reference pattern can be coupled to the membrane, and moving the at least one optical fiber can include moving the digit extension relative to the membrane.

In another aspect, an examination device is provided that includes an inflatable membrane defining an enclosed volume, and a substrate coupled to an interior surface of the membrane and having a plurality of reference lines formed on the substrate and arranged along a measurement axis. The substrate can be configured such that, when the inflatable membrane is inflated, a spacing between the plurality of reference lines remains constant.

The indicia can be printed on the substrate. The substrate can include or be formed of polyethylene. The substrate can be attached to the membrane only along a central axis of the substrate. The central axis can extend perpendicular to the measurement axis. The substrate can be attached to the membrane only at a center point of the substrate. The substrate can be attached to the membrane using at least one of an adhesive and a weld. The substrate can have a thickness between about 0.5 mils and about 6.0 mils. The substrate can have a thickness of about 2 mils. The device can include an optical fiber extending into the enclosed volume defined by the membrane. The membrane can be disposed over a digit extension of a glove.

In another aspect, a method of manufacturing an examination device is provided that includes attaching a substrate to a membrane such that the membrane is stretchable independently from the substrate, the substrate having a reference pattern comprising a plurality of indicia formed on the substrate and spaced along a measurement axis. The method can include positioning the membrane over a digit extension of a glove configured to be removably disposed around a human hand, and sealing a perimeter of the membrane to the glove such that the digit extension is independently movable relative to the reference pattern.

The substrate can be attached to the membrane only along a central axis of the substrate, the central axis extending perpendicular to the measurement axis. The indicia can be printed on the substrate. The substrate can be attached to the membrane only at a center point of the substrate. The substrate can be attached to the membrane using at least one of an adhesive and a weld. The method can include coupling an optical fiber to the glove such that a terminal end of the optical fiber extends between the membrane and the glove.

In another aspect, a method of measuring a prostate is provided that includes positioning a membrane in proximity to a rectal wall adjacent a prostate. The method can include inflating the membrane such that the membrane contacts the rectal wall, wherein a substrate attached to an interior surface of the membrane has a plurality of reference lines formed thereon, the reference lines defining a space therebetween that remains constant as the membrane is inflated. The method can include moving at least one optical fiber extending into an interior volume of the membrane across the plurality of reference lines to generate information indicative of a distance traveled by the at least one optical fiber.

The membrane can be disposed around a digit extension of a glove, and inflating the membrane can expand an interior volume between the glove and the membrane.

In another aspect, an examination device is provided that includes a glove configured to be removably disposed over a human hand, a membrane disposed over a portion of the glove and defining an enclosed volume between the glove and the membrane, and a reference pattern comprising a plurality of indicia disposed on the membrane and arranged along a measurement axis.

The indicia can be printed on the membrane. The indicia can be printed on a substrate coupled to the membrane. A spacing between the plurality of indicia as measured along the measurement axis can be configured to remain constant upon inflation and deflation of the membrane. The plurality of indicia can include lines extending perpendicular to the measurement axis. The lines can be separated by spaces having a width as measured along the measurement axis that is equal to a width of the lines as measured along the measurement axis. The lines can be separated by spaces having a width as measured along the measurement axis that is less than half of a width of the lines as measured along the measurement axis. The device can include an optical fiber extending into the enclosed volume, the lines being separated by spaces having a width as measured along the measurement axis that is less than a diameter of the optical fiber. The lines can have a width as measured along the measurement axis of approximately 0.7 mm and the lines can be separated by spaces having a width as measured along the measurement axis of approximately 0.3 mm. The plurality of indicia can define a uniform series of alternating dark and light portions. The plurality of indicia can extend along a portion of the substrate having a width a measured along the measurement axis of about 2 inches and a height as measured along an axis perpendicular to the measurement axis of about 1.5 inches.

In another aspect, an examination device is provided that includes an inflatable membrane configured to be disposed over and sealed around a digit extension of a glove for a human hand, the membrane defining an enclosed volume. The device can include a non-inflatable substrate coupled to an interior surface of the inflatable membrane, the non-inflatable substrate having a reference pattern disposed thereon, the reference pattern comprising a plurality of indicia arranged along a measurement axis.

The plurality of indicia can extend substantially parallel to one another. The plurality of indicia can define a uniform series of alternating dark and light portions. The plurality of indicia can be separated by spaces having a width that is equal to a width of the lines. The plurality of indicia can be separated by spaces having a width that is less than half of a width of the lines. The device can include an optical fiber extending into the enclosed volume, the plurality of indicia being separated by spaces having a width that is less than a diameter of the optical fiber. The plurality of indicia can have a width of approximately 0.7 mm and the lines can be separated by spaces having a width of approximately 0.3 mm.

In another aspect, an examination device is provided that includes a membrane defining an interior volume, a reference pattern disposed within the interior volume of the membrane, an illumination fiber extending into the interior volume of the membrane and configured to transmit light to the reference pattern through an output window, a first receiving fiber extending into the interior volume of the membrane and configured to receive light reflected from the reference pattern through a first input window, and a second receiving fiber extending into the interior volume of the membrane and configured to receive light reflected from the reference pattern through a second input window.

The output window can be formed in a terminal distal end of the illumination fiber, the first input window can be formed in a terminal distal end of the first receiving fiber, and the second input window can be formed in a terminal distal end of the second receiving fiber. The output window, the first input window, and the second input window can be disposed adjacent to one another in a delta configuration. The reference pattern can include a plurality of indicia arranged along a measurement axis and the first input window and the second input window can be arranged in a line that is substantially parallel to the measurement axis. The plurality of indicia can include a series of lines spaced equally along the measurement axis. The illumination fiber, the first receiving fiber, and the second receiving fiber can be configured to transmit near infrared light. The illumination fiber, the first receiving fiber, and the second receiving fiber can each have a diameter of approximately 0.5 mm.

In another aspect, a method of measuring an object is provided that includes positioning a reference pattern in proximity to an object, the reference pattern comprising alternating light and dark spaces arranged along a measurement axis, and positioning an optical receiver comprising an illumination fiber and first and second receiver fibers over the reference pattern such that an output window of the illumination fiber is aimed at the reference pattern and such that an input window of the first receiving fiber and an input window of the second receiving fiber are disposed along a line that is substantially parallel to the measurement axis. The method can include moving the optical receiver along the line relative to the reference pattern, and detecting a change in direction of movement of the optical receiver by measuring the light received by the first receiving fiber in time relation to the light received by the second receiving fiber.

In another aspect, an examination device is provided that includes a glove having a digit extension, a membrane disposed over at least a portion of the digit extension, the membrane and the digit extension forming a closed volume therebetween, and a finger clip attached to the digit extension and disposed within the closed volume. The device can include at least one illumination optical fiber and at least one receiving optical fiber extending into the closed volume and through the finger clip, and an inflation tube extending into the closed volume and configured to introduce an inflation medium into the closed volume.

The finger clip can be attached to the digit extension such that it extends along a dorsal surface of the digit extension and down across a distal tip of the digit extension. The at least one illumination optical fiber and the at least one receiving optical fiber can extend through the inflation tube. The inflation tube can terminate proximal to a proximal end of the finger clip. The at least one illumination optical fiber and the at least one receiving optical fiber can extend through an open channel formed in the finger clip and through a tunnel oriented substantially perpendicular to the open channel. The at least one illumination optical fiber and the at least one receiving optical fiber can terminate at a distance from a distal end of the tunnel. The distance can be between about 0.25 mm and about 0.5 mm. The digit extension can be or can include a forefinger extension.

In another aspect, a method of making an examination device is provided that includes forming an open channel in a finger clip, wherein the finger clip is configured to be disposed on a user's finger, and forming a through hole in the finger clip approximately perpendicular to the open channel such that the through hole intersects the open channel and provides a working connection from the open channel to a distal end of the finger clip. The method can include positioning at least one fiber optic within the open channel and the through hole such that an optical window formed in a terminal distal end of the fiber optic is aimed in a direction configured to be perpendicular to a dorsal surface of a user's finger.

The at least one fiber optic can include at least one illumination fiber optic and at least one receiving fiber optic. The finger clip and the open channel can be formed by injection molding. The finger clip can be formed from injection molded, soft-durometer urethane. The method can include routing the at least one fiber optic through an inflation tube that terminates proximal to a proximal end of the finger clip.

In another aspect, a method of measuring an object is provided that includes positioning a digit extension of a glove around a user's hand such that a finger clip attached to the digit extension extends along a dorsal surface of a digit of the user's hand and down across a distal tip of the digit. The method can include positioning the digit extension in proximity to an object, inflating a membrane disposed around the digit extension to inflate the membrane relative to the digit extension and to position a reference pattern coupled to the membrane at a distance apart from a distal tip of the finger clip, and moving the distal tip of the finger clip relative to the reference pattern to generate information indicative of a distance traveled by the distal tip of the finger clip relative to the reference pattern.

In another aspect, a connector system is provided that includes a first connector body having proximal and distal ends, the distal end defining a first mating interface, a first fluid lumen extending through the first connector body from an opening at the proximal end of the first connector body to an opening formed in the first mating interface, and a first set of optical fibers extending through the first connector body and terminating at the first mating interface. The connector system can include a second connector body having proximal and distal ends, the proximal end defining a second mating interface, a second fluid lumen extending through the second connector body from an opening formed in the second mating interface to an opening at the distal end of the second connector body, and a second set of optical fibers extending through the second connector body and terminating at the second mating interface. The connector system can include a connector housing configured to maintain the first mating interface in alignment with the second mating interface such that the first set of optical fibers is in optical communication with the second set of optical fibers and the first fluid lumen is in fluid communication with the second fluid lumen.

The connector housing can be formed integrally with at least one of the first connector body and the second connector body. When mated, the first fluid lumen and the second fluid lumen can form a continuous fluid-tight passage having proximal and distal terminal ends. The first set of optical fibers can enter the fluid-tight passage at a location other than the proximal and distal terminal ends. The first set of optical fibers can extend through less than an entire length of the first fluid lumen. The second set of optical fibers can extend through the second fluid lumen and through a tube coupled to the distal end of the second connector body. The first set of optical fibers can extend from the proximal end of the first connector body into an interior of the first fluid lumen. The system can include a first key coupled to the first connector body and configured to cooperate with a corresponding recess formed in the connector housing such that the first connector body can only be inserted into the connector housing in one orientation. The system can include a first strain relief overmold disposable over the first connector body and a second strain relief overmold disposable over the second connector body.

In another aspect, an examination system is provided that includes a glove having a digit extension, a membrane disposed over at least a portion of the digit extension, the membrane and the digit extension forming a closed volume therebetween, and an inflation tube extending into the closed volume and configured to receive an inflation fluid for inflating the membrane. The system can include at least one optical fiber extending through the inflation tube and into the closed volume, and a connector coupled to a proximal end of the inflation tube, the connector including an inflation lumen extending from the inflation tube to a mating interface, wherein an optical opening of the at least one optical fiber terminates at the mating interface.

The system can include a first key coupled to the connector and configured to allow the connector to mate to a second connector in only one orientation.

In another aspect, an examination system is provided that includes an optical receiver coupled to at least one optical fiber, an inflation medium supply coupled to an inflation tube, and a connector coupled to a distal end of the inflation tube, the connector including an inflation lumen extending from the inflation tube to a mating interface, wherein an optical opening of the at least one optical fiber terminates at the mating interface.

The at least one optical fiber can enter the inflation lumen at a location within the connector. The system can include a light source coupled to the at least one optical fiber. The system can include at least one processor configured to interpret signals output from the optical receiver. The inflation medium supply can include at least one of a pump and a tank of compressed air.

In another aspect, a system for estimating the volume of a prostate is provided that includes a processor programmed to provide a sensor input module configured to receive information indicative of light reflected from a reference pattern as an optical fiber is moved across the reference pattern from a first prostate lateral margin to a second prostate lateral margin. The processor can be programmed to provide a distance measuring module configured to convert the received information into a prostate palpable surface width ($PS_W$), and a volume estimation module configured to estimate a volume (V) of the prostate based on the palpable surface width ($PS_W$).

The volume estimation module can estimate the volume (V) as $V=PS_W^3 \times k$, wherein k is a constant. The constant k can be between about 0.35 and about 0.45. The constant k can be about 0.3926991. The processor can be programmed to provide an error detection module configured to detect that a measurement error has occurred when the received information indicates that a direction of movement of the optical fiber changed during a measurement. The processor can be programmed to provide a display module configured to drive a display to display the estimated volume (V). The processor can be programmed to provide an inflation control module configured to actuate a pump or a control valve to inflate a membrane disposed around a digit extension of a glove to a predetermined pressure or with a predetermined volume of air. The processor can be programmed to provide an RFID interface module configured to receive information indicative of an RFID signature of a disposable unit and to determine whether the disposable unit is an authenticated disposable unit.

In another aspect, a method of estimating the volume of a prostate is provided that includes moving an optical fiber across a reference pattern from a first lateral margin of a prostate to a second lateral margin of the prostate to generate information indicative of light reflected from the reference pattern. The method can include using at least one processor to convert the generated information into a prostate palpable surface width ($PS_W$), and using the at least one processor to estimate a volume (V) of the prostate based on the palpable surface width ($PS_W$).

The method can include estimating the volume (V) as $V=PS_W^3 \times k$, wherein k is a constant. The constant k can be between about 0.35 and about 0.45. The constant k can be about 0.3926991. The method can include using the at least one processor to detect that a measurement error has occurred when the generated information indicates that a direction of movement of the optical fiber changed during a measurement. The method can include using the at least one processor to drive a display to display the estimated volume (V). The method can include using the at least one processor to actuate a pump or a control valve to inflate a membrane disposed around a digit extension of a glove to a predetermined pressure or with a predetermined volume of air. The method can include using the at least one processor to receive information indicative of an RFID signature of a disposable unit and to determine whether the disposable unit is an authenticated disposable unit.

The present invention further provides devices, systems, and methods as claimed.

BRIEF DESCRIPTION OF THE DRAWINGS

The invention will be more fully understood from the following detailed description taken in conjunction with the accompanying drawings, in which:

FIG. 7C is a schematic view of the position and orientation of optical fiber windows relative to a reference pattern;

FIG. 11A is a perspective view of a connector system;

FIG. 11C is a perspective view of a first connector body;

FIG. 11E is a perspective view of a connector system;

FIG. 11F is a perspective view of a second connector body;

DETAILED DESCRIPTION

Certain exemplary embodiments will now be described to provide an overall understanding of the principles of the structure, function, manufacture, and use of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Systems and methods are provided herein that generally involve measuring a prostate or other object. In some embodiments, a reference pattern is positioned adjacent to the object to be measured and light reflected from the reference pattern is measured or interpreted to estimate various attributes of the object, such as its volume. For example, a membrane can be sealed over a glove to form a closed volume. The closed volume can be configured to be expanded via an inflation tube, and a reference pattern can be disposed within the closed volume along with one or more optical fibers. In use, a user can put on the glove, position the membrane in proximity to a rectal wall overlying a prostate, and inflate the membrane. As the user slides their finger across the rectal wall, the optical fibers move relative to the reference pattern and a controller senses light reflected through the fibers from the reference pattern. The controller can calculate or estimate various attributes of the prostate based on the reflected light, such as the palpable surface width or volume.

System Overview

Figure 1:
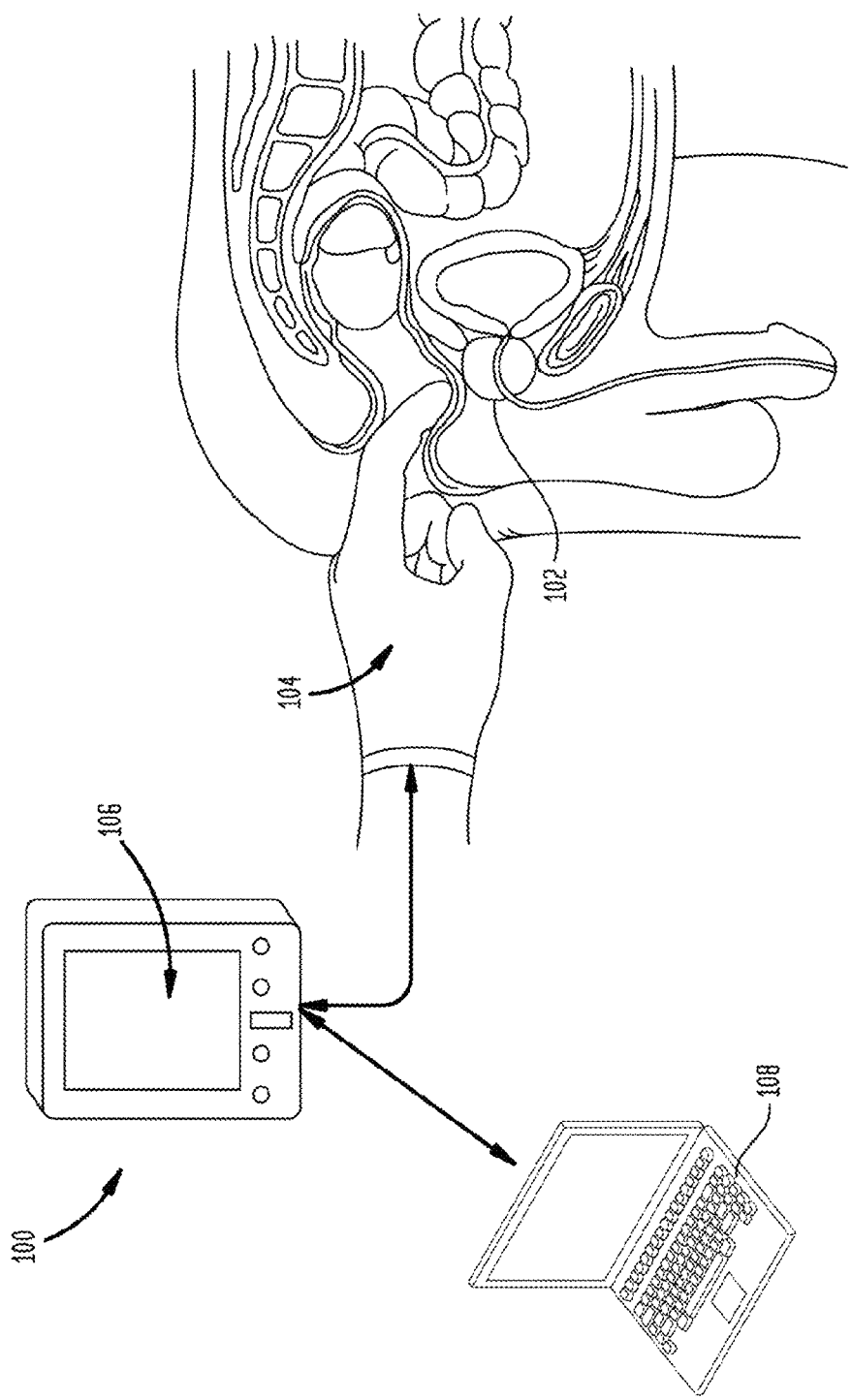
FIG. 1 is a schematic view of an examination system and a patient.

FIG. 1 illustrates an exemplary embodiment of an examination system 100 for measuring an object (e.g., a prostate 102). The system 100 can include a measurement assembly 104 configured to provide information indicative of a dimension of the object to a controller 106. The controller 106 can be configured to estimate one or more properties or conditions of the object based on the information provided by the measurement assembly 104. The controller 106 can also be coupled to a computer system 108 for storing or further processing the information.

Figure 2:
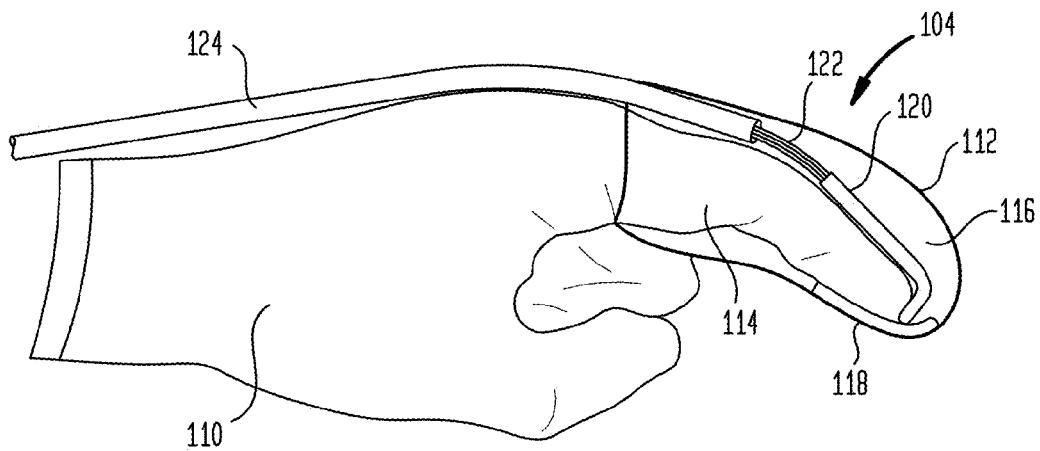
FIG. 2 is a partially-transparent side view of a measurement assembly.

As shown in FIG. 2, the measurement assembly 104 can include a glove 110 with a membrane 112 disposed over a digit extension 114 thereof to define a closed volume 116 between the glove 110 and the membrane 112. A reference pattern 118 can be formed on or coupled to an interior surface of the membrane 112 such that the reference pattern is disposed within the closed volume 116. The assembly 104 can also include a finger clip 120 coupled to the digit extension 114 beneath the membrane 112. One or more optical fibers 122 can be mounted in a channel or lumen formed in the finger clip 120. The optical fibers 122 can be configured to transmit light generated by a light source in the controller 106 to the reference pattern 118, and to transmit light reflected from the reference pattern to an optical sensor in the controller. The assembly 104 can also include an inflation tube 124 extending into the closed volume 116 and configured to supply an inflation medium to the closed volume to inflate the membrane 112 and expand the closed volume, or to extract an inflation medium from the closed volume to deflate the membrane 112 and reduce the closed volume. The optical fibers 122 can extend through the inflation tube 124, and a suitable connector can be provided at a proximal end of the inflation tube for coupling the inflation tube and the optical fibers to the controller 106. In some embodiments, the measurement assembly 104 can be disposable, e.g., adapted for a single use or for use with a single patient, whereas the controller 106 can be reusable.

In an exemplary method of operation, the measurement assembly 104 can be worn by a user (e.g., disposed over the user's hand). The user can then position the membrane 112 in proximity to an area to be measured (e.g., a patient's rectal wall, adjacent the prostate). The membrane can be inflated using the controller 106. With the membrane 112 remaining substantially stationary and the light source activated, the user can swipe their gloved finger and the finger clip 120 attached thereto from a first lateral margin of the prostate to a second lateral margin of the prostate. As the finger clip 120 moves across the prostate, light reflected from the reference pattern 118 can be transmitted to the controller 106, where it can be processed to determine or estimate various properties of the prostate, such as the palpable surface width of the prostate or the volume of the prostate.

Measurement Assembly

Glove

Figure 3:
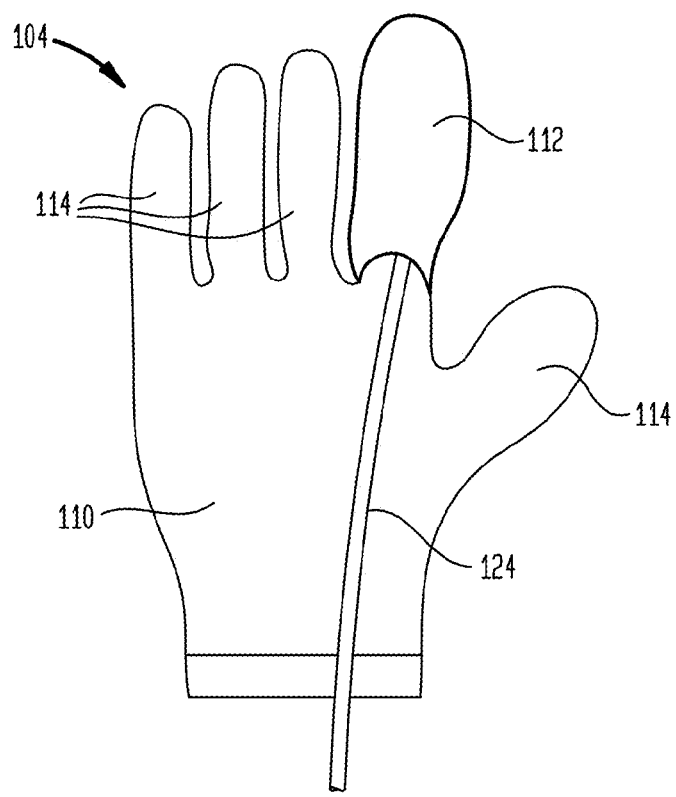
FIG. 3 is a top view of a measurement assembly.

FIG. 3 illustrates a top view of the measurement assembly 104. As shown, the measurement assembly 104 can include a glove 110 with one or more digit extensions 114 corresponding to, and configured to receive, the fingers of a human hand. The glove 110 can thus be configured to be removably disposed around a human hand or a portion thereof. The glove 110 can be formed from any of a variety of materials suitable for use in a medical environment, including latex, natural rubber latex, neoprene, nitrile, vinyl, Vytex, and so forth. In some embodiments, the glove 110 can be a standard exam glove or surgical glove. In the illustrated embodiment, a complete glove is shown (e.g., a glove having five digit extensions and configured to envelop the entirety of a human hand). It will be appreciated, however, that in some embodiments less than a complete glove can be used. For example, the glove can be in the form of a finger cot configured to cover only a single finger or portion thereof. In other embodiments, the glove can be omitted altogether and the membrane 112 can be sealed directly around the user's finger.

Membrane

The membrane 112 can be disposed over a portion of the glove 110 (e.g., one or more digit extensions 114 thereof), or can be disposed over the entirety of the glove 110. In some embodiments, the membrane 112 can be defined by a finger cot having an elongate tubular structure with a closed distal end and an open proximal end. The membrane 112 can be positioned over a digit extension 114 of the glove 110, such as the forefinger digit extension, and the open proximal end of the membrane can be sealed circumferentially around the digit extension. The membrane 112 can be sealed to the glove 110 using any of a variety of techniques, including UV-curable and/or biocompatible cements or adhesives. Exemplary adhesives include Dymax 1202-M-SC and Dymax 222/450 (available from Dymax Corporation of Torrington, Conn.). The membrane 112 can be sealed to the glove 110 such that a closed, fluid-tight volume 116 is defined between the membrane and the glove. As discussed in further detail below, the inflation tube 124 can be sealed between the membrane 112 and the glove 110, such that the inflation tube extends into the closed volume 116 and a distal outlet of the inflation tube is disposed within the closed volume. The membrane 112 can be configured to expand or inflate when an inflation medium is supplied through the inflation tube 124, and to contract or deflate when an inflation medium is removed through the inflation tube. Like the glove 110, the membrane 112 can be formed from any of a variety of materials suitable for use in a medical environment, including latex, natural rubber latex, neoprene, nitrile, vinyl, Vytex, and so forth. In some embodiments, the membrane 112 is formed form the same material as the glove 110 and is configured to withstand strain forces applied thereto during inflation.

Reference Pattern

Figure 4A:
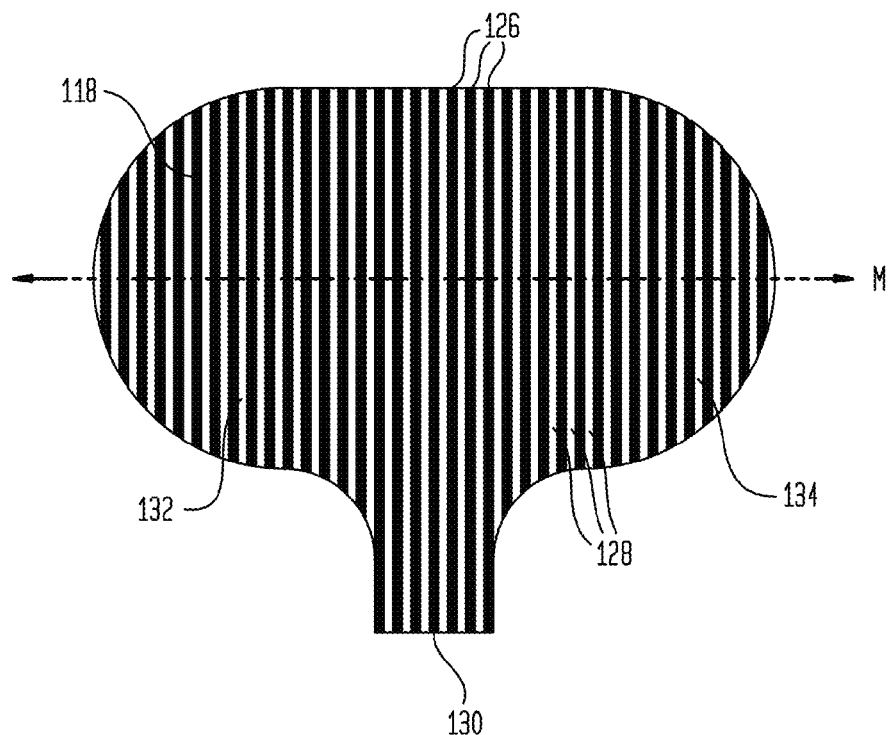
FIG. 4A is a top view of a reference pattern.
Figure 4B:
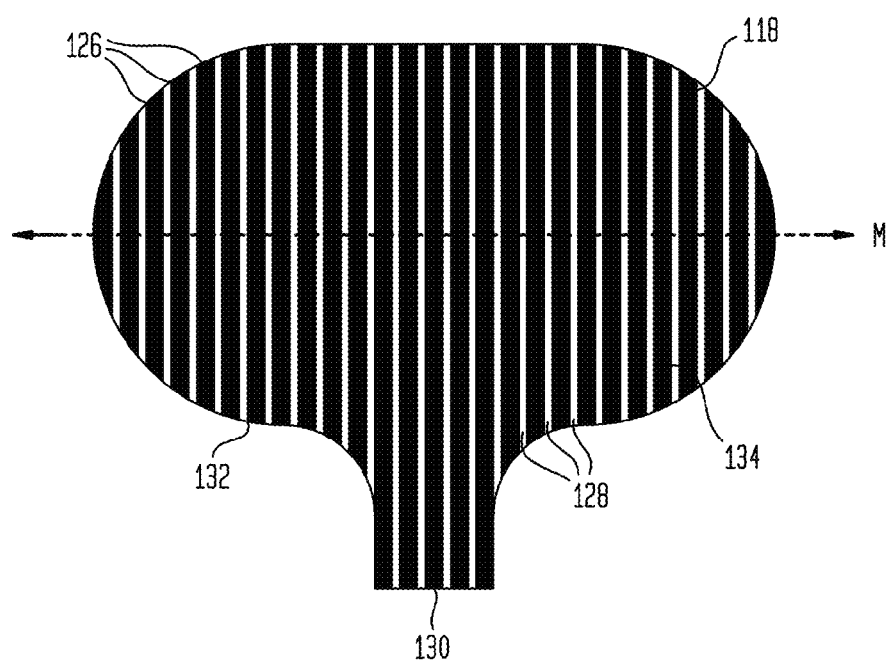
FIG. 4B is a top view of another reference pattern.

The reference pattern 118 can include any of a variety of indicia to provide a reference scale for measuring a dimension of an object. FIG. 4A illustrates an exemplary embodiment of a reference pattern 118 in which the indicia include a plurality of equally-spaced, parallel lines 126 defining alternating light and dark regions. In other words, the indicia provide a uniform series of alternating dark and light portions. The parallel lines 126 are arranged along a measurement axis M and extend perpendicular thereto. In the embodiment of FIG. 4A, the lines 126 have a width as measured along the measurement axis M that is equal to the width of the spaces 128 along the measurement axis. It will be appreciated, however, that any of a variety of spacing widths can be used. For example, as shown in FIG. 4B, the spaces 128 can have a width as measured along the measurement axis M that is less than half of the width of the lines 126 as measured along the measurement axis.

In operation, light reflected from the reference pattern 118 can be received though an input window formed in an optical fiber. In some embodiments, it can be desirable for the width of the light regions 128 of the reference pattern 118 to be less than the diameter or width of the optical fiber input window. This can advantageously prevent the fiber from receiving light reflected from a plurality of light regions 128 at the same time, and can thereby make pattern boundary crossings easier to identify from the sensor output data. Thus, in embodiments in which the optical fiber has an input window with a diameter of approximately 0.5 mm, the reference pattern 118 can include light regions 128 having a width as measured along the measurement axis M of about 0.3 mm and dark regions 126 having a width as measured along the measurement axis of about 0.7 mm.

The size and shape of the reference pattern 118 can vary depending on application (e.g., the size and shape of the user's hand, or the size and shape of the object to be measured). In the illustrated embodiment, the reference pattern 118 includes an elongate central portion 130 with first and second wing portions 132, 134 extending laterally therefrom. The wing portions 132, 134 can be sized and configured to wrap around the user's finger when the membrane 112 is in a deflated state, and to at least partially unroll therefrom when the membrane is in an inflated state. In some embodiments, the reference pattern 118 can have a width as measured along the measurement axis M of about 2 inches and a height as measured perpendicular to the measurement axis of about 1.5 inches.

The reference pattern 118 can be formed directly on the interior surface of the membrane 112, or can be formed on a separate substrate 136 coupled to the interior surface of the membrane. In embodiments in which the reference pattern 118 is formed directly on the interior of the membrane 112, inflation of the membrane can result in stretching or distortion of the reference pattern to a degree commensurate with the degree of inflation of the membrane. In such cases, unless the degree of membrane inflation is known and well-controlled, the stretching of the reference pattern 118 can undesirably introduce error into the measurement provided by the evaluation system 100.

Figure 5A:
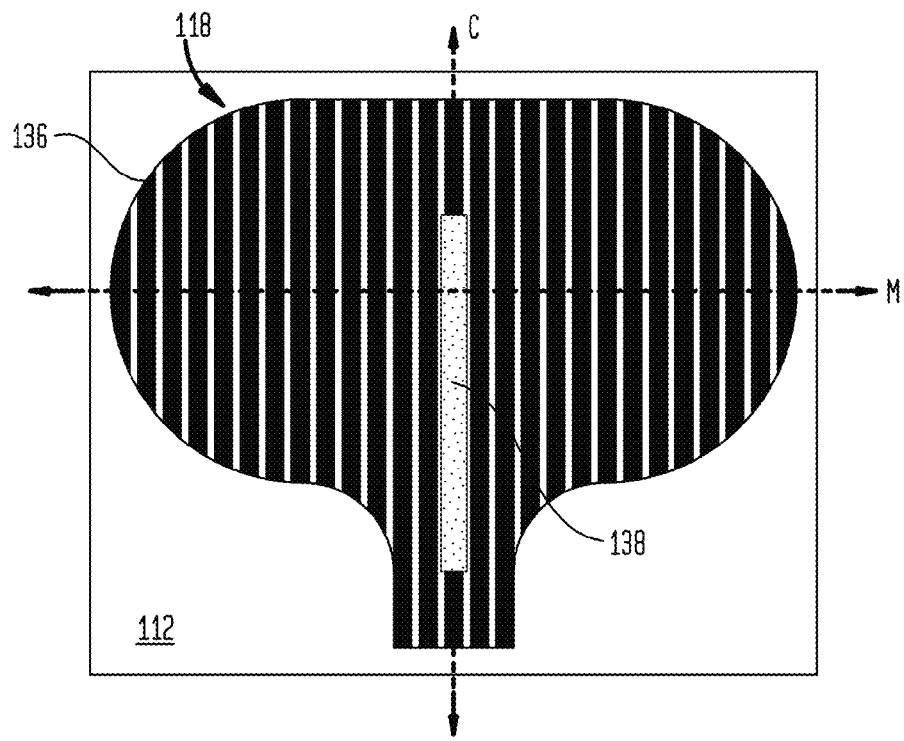
FIG. 5A is a top view of a reference pattern adhered to a membrane along a line.
Figure 5B:
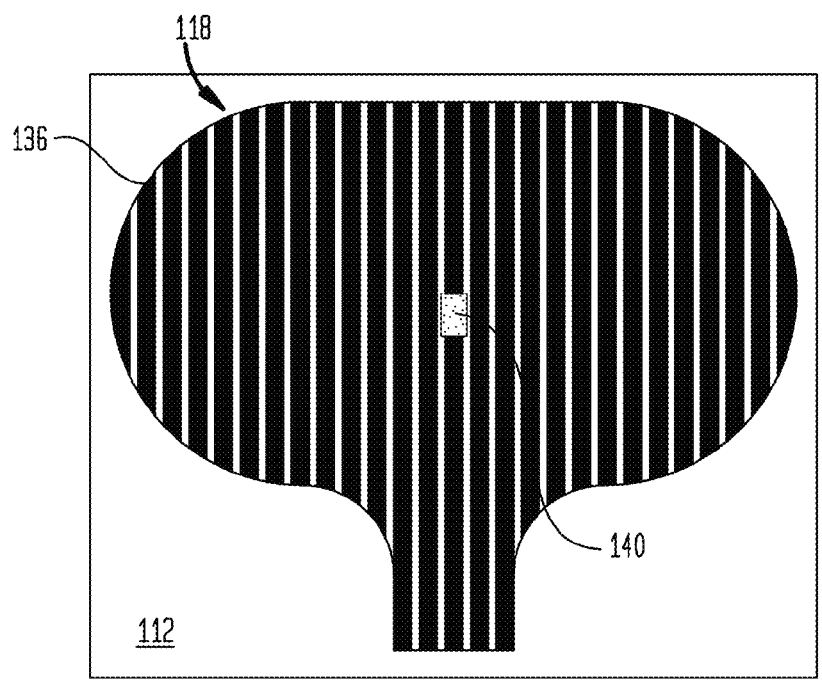
FIG. 5B is a top view of a reference pattern adhered to a membrane at a single point.
Figure 6A:
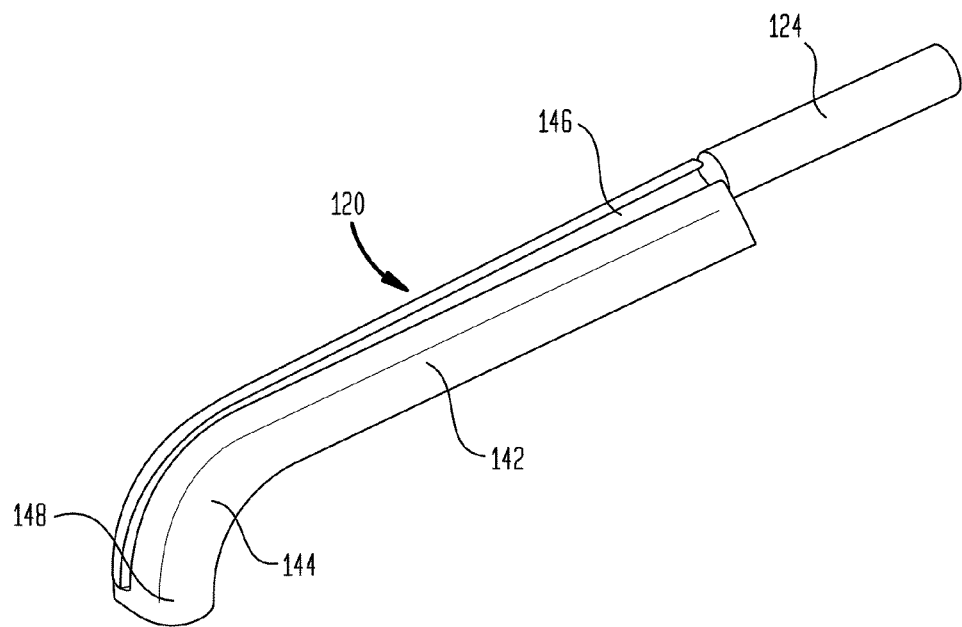
FIG. 6A is a perspective view of a finger clip.
Figure 6B:
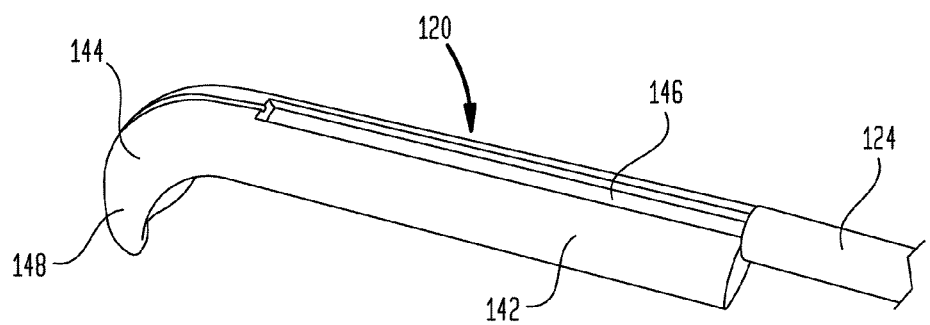
FIG. 6B is another perspective view of a finger clip.
Figure 6C:
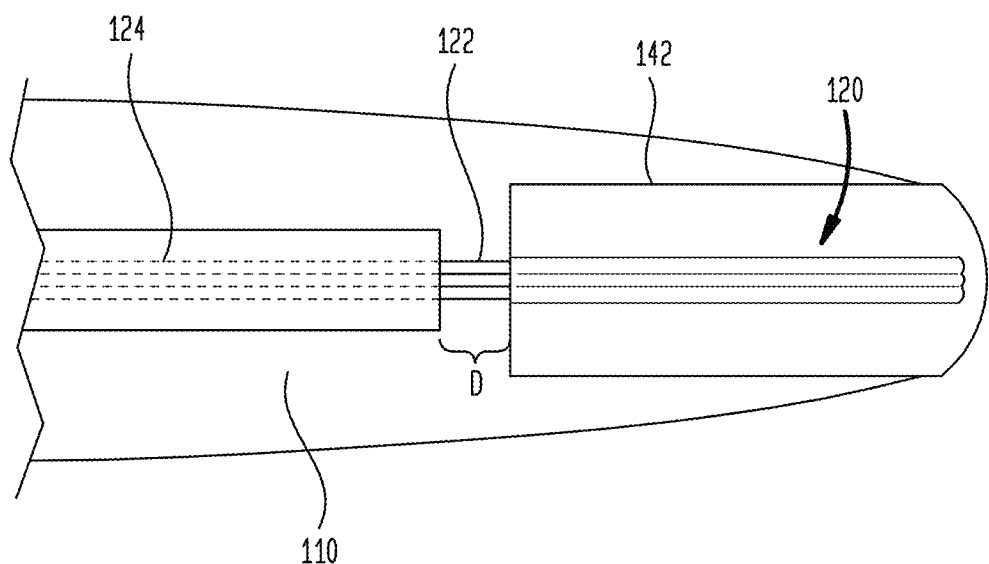
FIG. 6C is a top view of a finger clip attached to a glove.
Figure 6D:
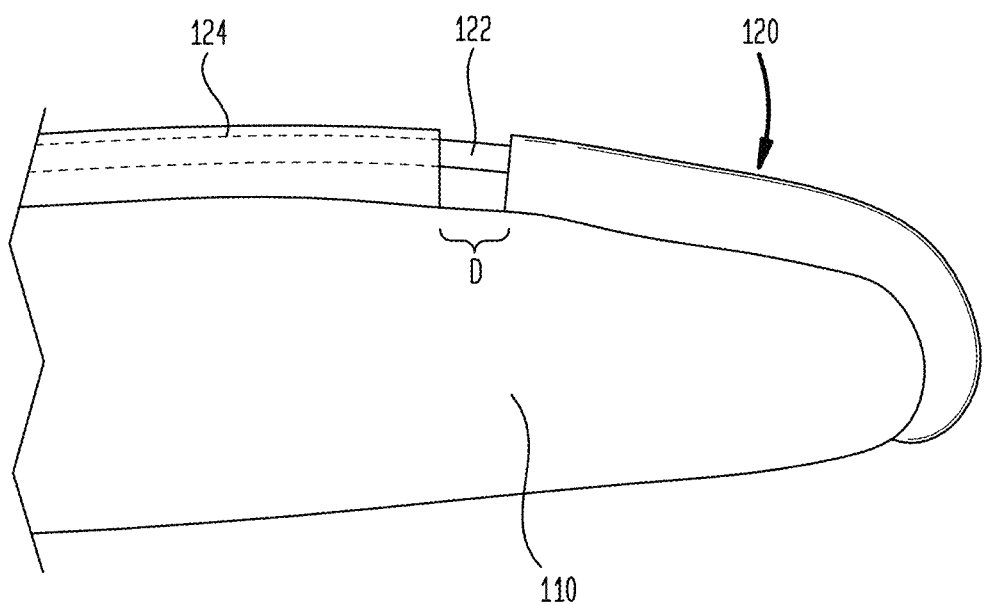
FIG. 6D is a side view of a finger clip attached to a glove.

Accordingly, in some embodiments, the reference pattern 118 can be formed on a substrate 136 that is separate from but coupled to the membrane 112 such that the dimensions of the reference pattern are not distorted by inflation or deflation of the membrane. In other words, the reference pattern 118 does not inflate or deflate or otherwise distort with the membrane 112, and instead the spacing 128 between the plurality of indicia 126, and the width of the indicia 126, can remain constant upon inflation and deflation of the membrane 112. As shown in FIGS. 5A-5B, the reference pattern 118 can be formed on a substrate 136 separate from the membrane 112. The substrate 136 can be attached to the membrane 112 using an adhesive or other attachment techniques, such as fusion bonding, hot-gas welding, vibration welding, solvent bonding, or ultrasonic welding. In the embodiment of FIG. 5A, a line 138 of adhesive is applied along a central axis C of the substrate 136 (e.g., an axis that is perpendicular to the measurement axis M). It will be appreciated that, due to this adhesive pattern, any stretching of the substrate 136 as the membrane 112 is inflated or deflated will only stretch the reference pattern 118 along the central axis C, and not along the measurement axis M. Accordingly, the spacing 128 between the measurement lines 126 can remain constant during inflation and deflation, as can the width of the lines 126. In the embodiment of FIG. 5B, the substrate 136 is adhered to the membrane 112 at a single discrete point 140 (e.g., at a center point of the substrate 136). The size and location of the adhesion point 140 can be selected to balance resistance to inflation-related distortion of the reference pattern 118 with resistance to inadvertent rotation of the substrate 136 relative to the membrane 112.

The reference pattern 118 can be formed on the substrate 136 or membrane 112 in any of a variety of ways. In some embodiments, the dark regions 126 of the reference pattern 118 are printed on the substrate 136 or membrane 112, for example using dark-colored ink, dye, or paint. The light regions 128 of the reference pattern 118 can be formed by untreated portions of the substrate 136 or membrane 112, in which case they can have the same color, transparency, translucency, etc. as the underlying material. The light regions 128 can also be printed on the membrane 112 or substrate 136, for example using light-colored ink, dye, or paint. In embodiments in which the light regions 128 are formed by untreated portions of the substrate 136 or membrane 112, light can reflect off of the substrate or membrane itself, or off of the tissue or other object underlying the substrate or membrane.

Any of a variety of suitable materials can be used for the substrate 136, including plastics such as polyethylene. In some embodiments, the substrate 136 can have a thickness between about 0.5 mils and about 6.0 mils. In some embodiments, the substrate 136 can have a thickness of about 2 mils.

Finger Clip and Inflation Tube

FIGS. 6A-6D illustrate an exemplary embodiment of the finger clip 120 and the inflation tube 124. The finger clip can be configured to hold one or more optical fibers 122 in a fixed position relative to the user's finger, in a fixed position relative to one another, and/or in a fixed alignment relative to the reference pattern 118.

As shown, the finger clip 120 can include an elongate body 142 configured to substantially conform to the dorsal surface of a user's finger (or a user's gloved finger as the case may be). The elongate body 142 can include a curved or bent distal portion 144 configured to substantially conform to the distal tip of the user's finger. Thus, the finger clip 120 can be attached to the digit extension 114 of the glove 110 such that it extends along a dorsal surface of the digit extension and down across a distal tip of the digit extension. It will be appreciated that the finger clip 120 can be adhered or otherwise attached to the glove 110, such that the finger clip remains in a fixed position relative to a user's finger when the glove is worn by the user.

The finger clip 120 can include one or more paths through which one or more optical fibers 122 can be routed. For example, the finger clip 120 can include an open channel 146 formed in its dorsal surface. The finger clip 120 can also include a tunnel 148 formed in at least a portion of the curved distal part 144 of the finger clip, extending substantially perpendicular to the dorsal surface of the finger clip, from the open channel 146 to an opening 150 (see FIGS. 7A-7B) defined by the terminal distal end of the tunnel 148. While an open channel 146 in combination with a closed tunnel 148 is shown, it will be appreciated that the optical fiber path through the finger clip 120 can also be open along its entire length, closed along its entire length, or can include any combination of closed and open portions. The finger clip 120 can be formed from a variety of materials and using a variety of techniques. In some embodiments, the finger clip 120 can be injection molded from a soft durometer urethane (e.g., a 20 durometer urethane). The length of the finger clip 120 can be chosen such that, when the distal tip of the finger clip is placed in proximity to the rectal wall over the prostate, the proximal tip of the finger clip is fully disposed within the rectum and the inflation tube 124 extends distally beyond the anal ring. This can advantageously prevent the anal ring from pinching the membrane 112 between the distal end of the inflation tube 124 and the proximal end of the finger clip 120, which could prevent full inflation of the membrane. In some embodiments, the finger clip 120 can have a length of about 4 cm.

The finger clip 120 can be disposed entirely within the closed volume 116 defined between the membrane 112 and the glove 110, such that its proximal end is adjacent to the distal outlet of the inflation tube 124. The inflation tube 124 can terminate a distance D from the proximal end of the finger clip 120, such that inflation media directed through the inflation tube 124 can exit the tube at its distal end and enter the closed volume 116 without being obstructed by the finger clip 120. The inflation tube 124 can be formed by a length of tubing, such as Tygon ND Series medical tubing or S-50-HL Tygon tubing available from Saint-Gobain S.A. of France. In an exemplary embodiment, the inflation tube 124 has an inside diameter of $3/32$ inches and an outside diameter of $5/32$ inches. The length of the inflation tube 124 can be selected based on a variety of factors, including user preference and the typical distance between the controller 106 and the patient. In an exemplary embodiment, the inflation tube 124 has a length of about 1 meter. The inflation tube 124 can be configured to deliver an inflation medium to the closed volume 116, or to extract an inflation medium from the closed volume. Exemplary inflation media include air, carbon dioxide, saline, and water. In some embodiments, the finger clip 120 can be omitted and the fibers 122 and/or the inflation tube 124 can instead be attached directly to the glove 110, for example using an adhesive. The inflation tube 124 can have a circular cross-section, a rectangular-cross section, or any other cross-section that defines an inflation lumen through which inflation media can be conveyed.

Fibers

The measurement assembly 104 can include one or more optical fibers 122 configured to transmit light generated by a light source to the reference pattern 118, and/or to transmit light reflected from the reference pattern to an optical sensor. The optical fibers 122 can extend through the inflation tube 124 and can be routed through the fiber path defined by the finger clip 120. The optical fibers 122 can be secured within the fiber path, for example using a friction fit or a suitable adhesive. The fibers 122 can terminate a distance from the distal opening 150 in the finger clip tunnel 148, such that a desired spacing is maintained between the end of the fiber and the reference pattern 118 even when the tip of the finger clip 120 is in direct contact with the reference pattern. In some embodiments, the fibers 122 can terminate between about 0.25 mm and about 0.5 mm from the distal opening 150 of the finger clip tunnel 148. The fibers 122 can thus be positioned within the finger clip 120 such that optical windows formed in the terminal distal ends of the fibers are aimed in a direction perpendicular to a dorsal surface of a user's finger when the finger clip is attached to the user's finger.

Figure 7A:
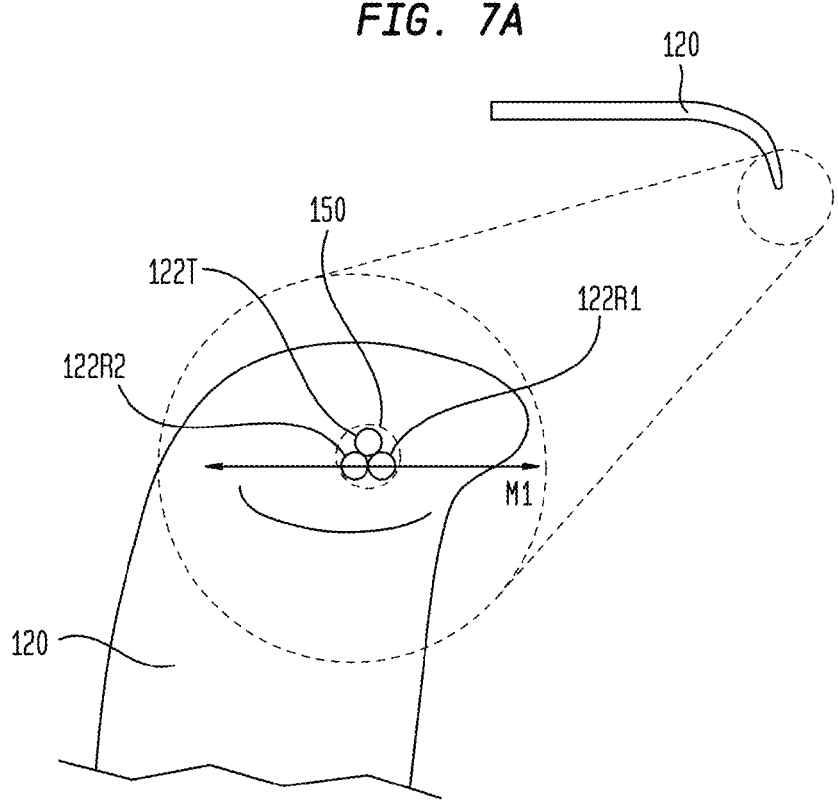
FIG. 7A is a schematic end view of a finger clip with optical fibers arranged in a triangle pattern.
Figure 7B:
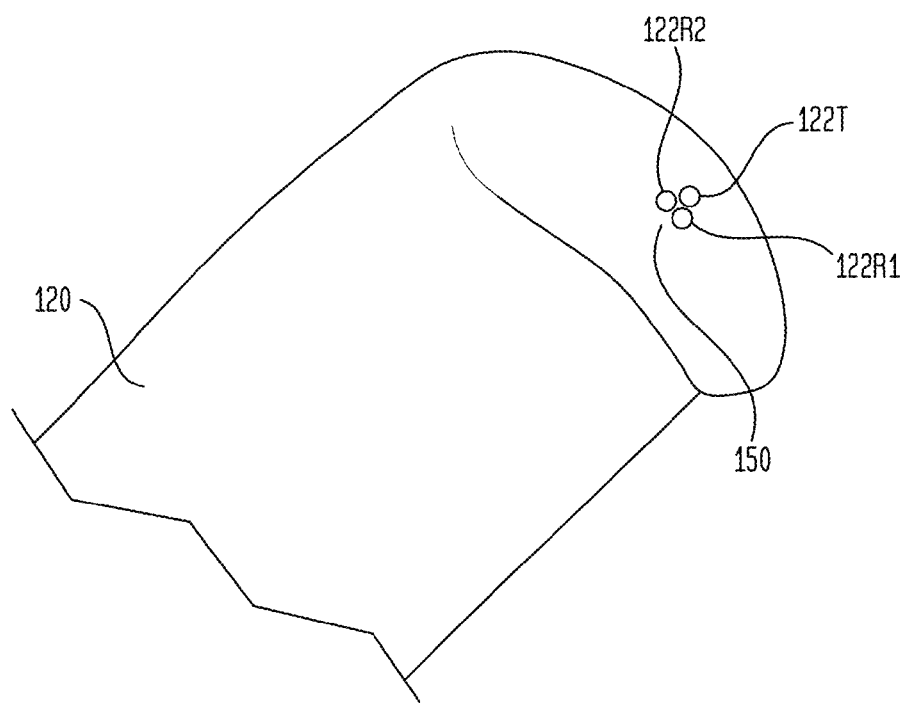
FIG. 7B is an end view of a finger clip with optical fibers arranged in a triangle pattern.

In some embodiments, a single fiber 122 can be used both to transmit light from the light source to the reference pattern 118 and to transmit light reflected from the reference pattern to the optical sensor. In further embodiments, the measurement assembly 104 can include a transmitting optical fiber for directing light from the light source to the reference pattern 118 and a receiving optical fiber for directing light reflected from the reference pattern to the optical sensor. In still further embodiments, as shown in FIGS. 7A-7C, the system can include a transmitting fiber 122T and first and second receiver fibers 122R1, 122R2, each of the receiver fibers being configured to transmit light reflected from the reference pattern 118 to one or more optical sensors. The optical fibers 122 can be coupled directly to the light source or optical sensors, or can be coupled thereto via one or more intermediate fibers, for example using a connector system as described below.

Each of the optical fibers 122 can be jacketed or unjacketed, and can include one or more input or output windows through which light can pass. For example, the transmitting optical fiber 122T can include an input window defined by its terminal proximal end and an output window defined by its terminal distal end. Similarly, the receiver fiber(s) 122R1, 122R2 can include an input window defined by their terminal distal end and an output window defined by their terminal proximal end. The fibers 122 can be configured to transmit infrared, near-infrared, visible, or other any other detectable spectra of light. Exemplary fibers include unjacketed CK-20 ESKA plastic optical fibers having a diameter of 0.5 mm, available from Mitsubishi International Corporation of New York, N.Y. The fibers 122 can have a length that is slightly longer than that of the inflation tube 124 to facilitate routing of the fibers through the finger clip 120 and/or a connector assembly coupled to the inflation tube.

As shown in FIGS. 7A-7C, the fibers 122 can be positioned in the finger clip 120 so as to improve the measurement accuracy and error detection capabilities of the system 100. In particular, the transmitting fiber 122T and the first and second receiver fibers 122R1, 122R2 can be positioned in the finger clip 120 such that the input windows of the first and second receiver fibers are arranged in a line M1 that is substantially parallel to the measurement axis M of the reference pattern 118 when the system 100 is assembled. The transmitting fiber 122T can be positioned above or below the receiver fibers 122R1, 122R2 such that the output window of the transmitting fiber and the input windows of the first and second receiver fibers are arranged in a triangle or delta pattern.

During operation, as the user swipes the finger clip 120 across the reference pattern 118, the offset between the receiver fibers 122R1, 122R2 along the measurement axis M can cause one of the receiver fibers to transmit reflected light before the reflected light can be transmitted by the other receiver fiber. Accordingly, the optical sensor output corresponding to the first fiber will toggle before the optical sensor output of the second fiber.

Figure 8A:
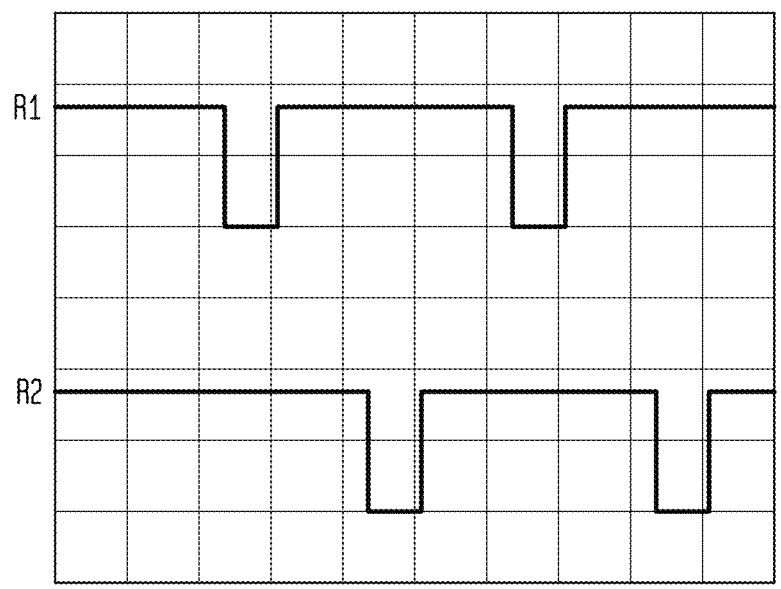
FIG. 8A is a plot of optical sensor output signals as a function of time when optical fibers are moved in a first direction relative to a reference pattern.
Figure 8B:
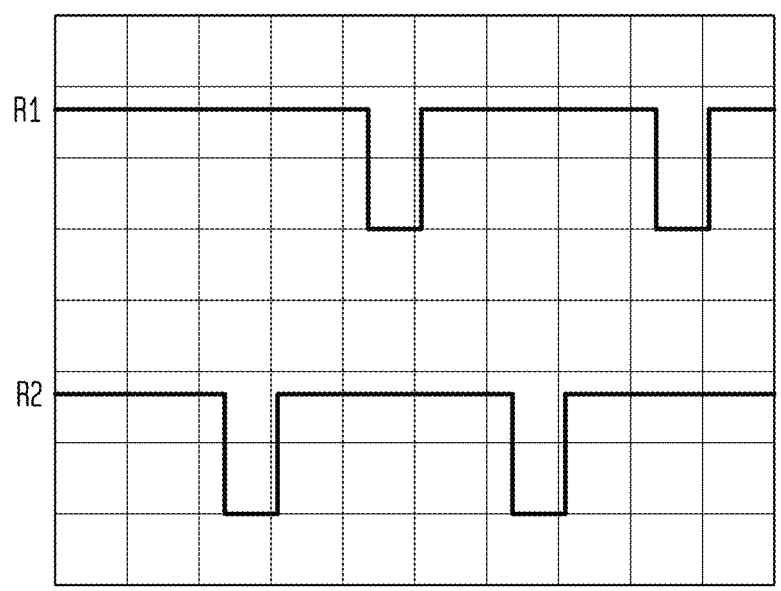
FIG. 8B is a plot of optical sensor output signals as a function of time when optical fibers are moved in a second direction, opposite to the first direction, relative to a reference pattern.

FIGS. 8A and 8B are plots of the output of an optical sensor R1 coupled to the first receiver fiber 122R1 and the output of an optical sensor R2 coupled to the second receiver fiber 122R2 as a function of time. As shown in FIG. 8A, when the finger clip 120 is moved in a first direction along the measurement axis M, the sensor R1 for the first receiver fiber 122R1 detects a boundary crossing slightly before the boundary crossing is detected by the sensor R2 for the second receiver fiber 122R2. As shown in FIG. 8B, when the finger clip 120 is moved in a second direction along the measurement axis M, opposite to the first direction, the sensor R2 for the second receiver fiber 122R2 detects a boundary crossing slightly before the boundary crossing is detected by the sensor R1 for the first receiver fiber 122R1. Accordingly, by comparing the light received by the first receiver fiber 122R1 in time relation to the light received by the second receiver fiber 122R2, the direction of finger clip 120 movement relative to the reference pattern 118 can be determined. As discussed further below, the controller 106 can be configured to detect that an error has occurred when a change in direction is detected, or to compensate for the change in direction.

Controller

Figure 9A:
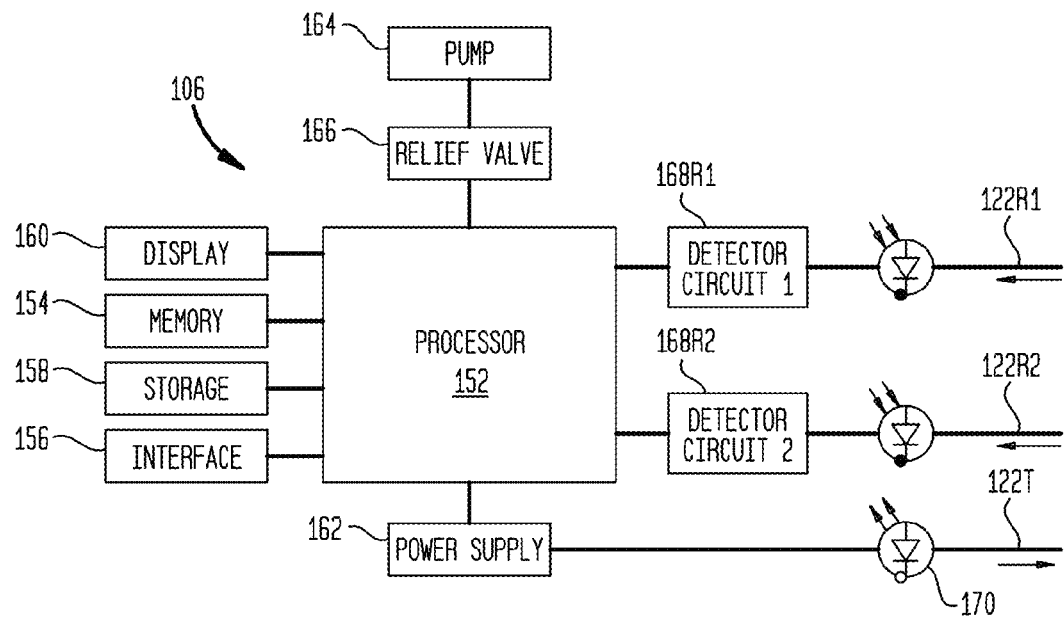
FIG. 9A is a schematic diagram of the physical components of a controller.

FIG. 9 illustrates a block diagram of the physical components of an exemplary embodiment of the controller 106. Although an exemplary controller 106 is depicted and described herein, it will be appreciated that this is for sake of generality and convenience. In other embodiments, the controller 106 may differ in architecture and operation from that shown and described here.

The illustrated controller 106 includes a processor 152 which controls the operation of the controller 106, for example by executing embedded software, operating systems, device drivers, application programs, and so forth. The processor 152 can include any type of microprocessor or central processing unit (CPU), including programmable general-purpose or special-purpose processors and/or any of a variety of proprietary or commercially-available single or multi-processor systems, including 32-bit PIC Peripheral Interface Controllers or 16-bit dsPIC digital signal Peripheral Interface Controllers available from Microchip Technology Incorporated of Chandler, Ariz. As used herein, the term processor can refer to microprocessors, microcontrollers, ASICs, FPGAs, processors that read and interpret program instructions from internal or external memory or registers, and so forth. The controller 106 also includes a memory 154, which provides temporary or permanent storage for code to be executed by the processor 152 or for data that is processed by the processor. The memory 154 can include read-only memory (ROM), flash memory, one or more varieties of random access memory (RAM), and/or a combination of memory technologies. The various components of the controller 106 can be interconnected via any one or more separate traces, physical busses, communication lines, etc.

The controller 106 can also include an interface 156, such as a communication interface or an I/O interface. A communication interface can enable the controller 106 to communicate with remote devices (e.g., other controllers or computer systems) over a network or communications bus (e.g., a universal serial bus). An I/O interface can facilitate communication between one or more input devices, one or more output devices, and the various other components of the controller 106. Exemplary input devices include touch screens, mechanical buttons, keyboards, and pointing devices. The controller can also include a storage device 158, which can include any conventional medium for storing data in a non-volatile and/or non-transient manner. The storage device 158 can thus hold data and/or instructions in a persistent state (i.e., the value is retained despite interruption of power to the controller 106). The storage device 158 can include one or more hard disk drives, flash drives, USB drives, optical drives, various media disks or cards, and/or any combination thereof and can be directly connected to the other components of the controller 106 or remotely connected thereto, such as through the communication interface. The controller 106 can also include a display 160, and can generate images to be displayed thereon. In some embodiments, the display 160 can be a vacuum fluorescent display (VFD), an organic light-emitting diode (OLED) display, or a liquid crystal display (LCD).

The controller 106 can also include a power supply 162 and appropriate regulating and conditioning circuitry. Exemplary power supplies include batteries, such as polymer lithium ion batteries, or adapters for coupling the controller 106 to a DC or AC power source (e.g., a USB adapter or a wall adapter). The controller 106 can also include an inflation system 164, such as an electromechanical pump controlled by the processor 152. Other inflation systems can also be employed, such as a stored volume of compressed fluid (e.g., air or carbon dioxide) or a manual pump (e.g., a sphygmomanometer bulb). A pressure relief valve 166 or other safety device can also be provided to prevent overinflation of the membrane 112 and/or to deflate the membrane when an evaluation is complete. In some embodiments, the pressure relief valve 166 can be configured to fail into the open position, such that pressure is released from the membrane 112 in the event of a power loss or other system malfunction. The inflation system 164 can be configured to supply an inflation medium through the inflation tube 124 and into the closed volume 116. Any of a variety of inflation media can be used, including air, carbon dioxide, saline, water, and the like. In some embodiments, the inflation system 164 can be configured to inflate the membrane 112 to an inflation pressure of 1.5 psi, and the pressure relief valve 166 can be configured to release pressure if and when it exceeds 2.0 psi. The inflation system 164 can also be configured to supply a fixed volume of an inflation medium to the membrane 112, e.g., about 25 mL of air.

The controller 106 can also include an optical system that includes a first detector circuit 168R1 for receiving light transmitted through the first receiver fiber 122R1, a second detector circuit 168R2 for receiving light transmitted through the second receiver fiber 122R2, and a light source 170 for producing light to be transmitted through the transmitting fiber 122T. In some embodiments, the detector circuits 168 can include a photo detector that is optically coupled to a fiber 122 and electrically coupled to the processor 152. Exemplary photo detectors include CMOS image sensors, charge-coupled devices, photodiodes, photoresistors, and phototransistors (e.g., photodarlington detectors). The photo detector can provide an electrical output signal to the processor 152 based on light that is received by the photo detector. The light source 170 can be or can include any of a variety of devices configured to produce light, including LEDs and incandescent bulbs. In some embodiments, the light source 170 can include an infrared LED.

Figure 9B:
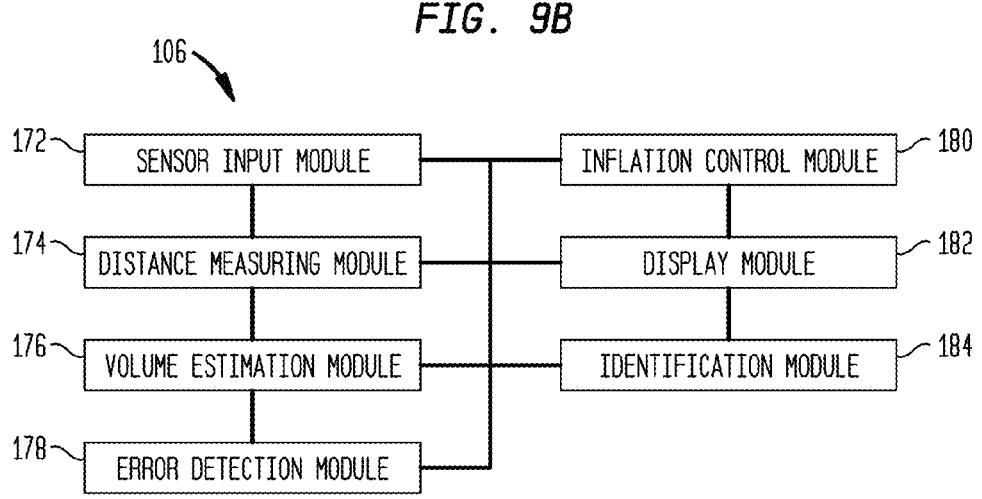
FIG. 9B is a schematic diagram of the logical components of a controller.

The various functions performed by the controller 106 can be logically described as being performed by one or more modules. It will be appreciated that such modules can be implemented in hardware, software, or a combination thereof. It will further be appreciated that, when implemented in software, modules can be part of a single program or one or more separate programs, and can be implemented in a variety of contexts (e.g., as part of an embedded software package, an operating system, a device driver, a standalone application, and/or combinations thereof). In addition, software embodying one or more modules can be stored as an executable program on one or more non-transitory computer-readable storage mediums. Functions disclosed herein as being performed by a particular module can also be performed by any other module or combination of modules, and the controller can include fewer or more modules than what is shown and described herein. FIG. 9B is a schematic diagram of the modules of one exemplary embodiment of the controller 106.

As shown in FIG. 9B, the controller 106 can include a sensor input module 172 configured to receive information indicative of light reflected from the reference pattern 118 as the optical fiber(s) 122 are moved across the reference pattern during an examination. The sensor input module 172 can read and interpret photo detector output signals supplied from the photo detectors 168 to the processor 152, e.g., via a general purpose input/output pin of the processor. The sensor input module 172 can optionally perform various processing on the photo detector output signal, such as debouncing, analog-to-digital conversion, filtering, and so forth.

The controller 106 can also include a distance measuring module 174 configured to convert the information received by the sensor input module 172 into a measurement of the object being evaluated (e.g., a palpable surface width $PS_W$ in the case of a prostate). For example, when a start instruction is issued (e.g., in response to the user's pressing of a "start measurement" button or equivalent), the distance measuring module 174 can begin counting the number of signal pulses received from the photo detectors 168. When an end instruction is issued (e.g., in response to the user's pressing of an "end measurement" button or after a predetermined time has elapsed without a detected pulse), the distance measuring module 174 can multiply the number of pulses counted by the width of the indicia 126 and spaces 128 formed on the reference pattern 118. This width can be pre-stored as a constant value in the memory 154 of the controller 106, can be manually input by the user via the controller's user interface, or can be read from a passive or active memory chip disposed in the measurement assembly 104.

Figure 10:
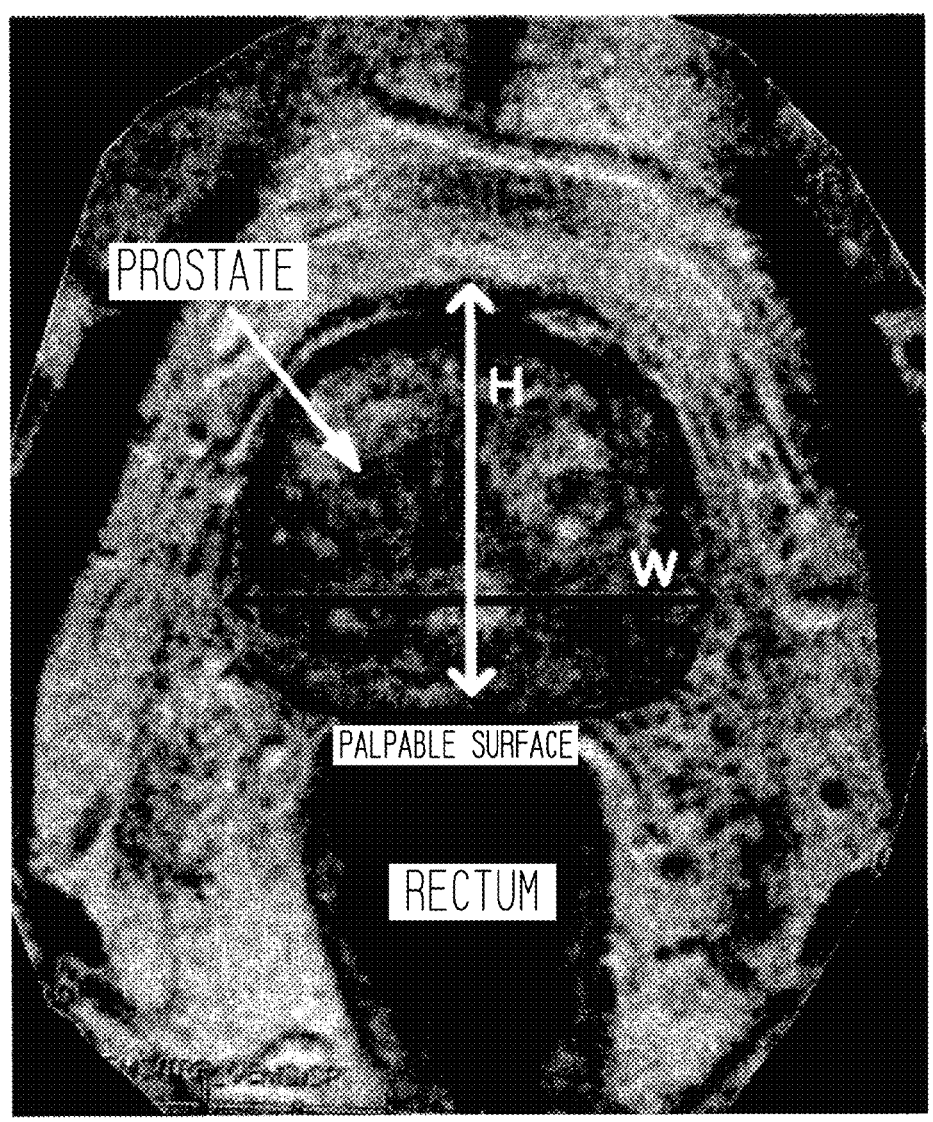
FIG. 10 is a magnetic resonance image of a prostate.

The controller 106 can also include a volume estimation module 176 configured to estimate a volume or other attribute of the object being measured based on one or more measurements obtained by the distance measuring module 174. For example, the volume estimation module 176 can be configured to calculate or estimate the volume (V) of a prostate based on the palpable surface width ($PS_W$) of the prostate as obtained by the distance measuring module 174. The palpable surface of a prostate is illustrated in the magnetic resonance image shown in FIG. 10. The volume can be calculated as:

$$V = PS_W^3 \cdot k$$

where k is a constant. Any of a variety of values can be used for the constant k to calculate the volume. In some embodiments, k is between about 0.01 and about 1.00. In some embodiments, k is between about 0.35 and about 0.45. In some embodiments, k is about 0.3926991. The volume estimation module 176 can also use other techniques to estimate the volume (V) based on the measured palpable surface width $PS_W$. For example, the volume estimation module 176 can reference a lookup table stored in the memory 154 to determine a volume associated with a particular palpable surface width. The volume estimation module 176 can also estimate other dimensions of the prostate based on the palpable surface width (e.g., a height (H), a width (W) and a depth (D)), and calculate the prostate volume using the estimated dimensions. For example, the volume (V) of the prostate can be calculated as:

$$V = H \cdot W \cdot D \cdot \pi/6$$

or as:

$$V = H^2 \cdot W \cdot \pi/6$$

Referring again to FIG. 9B, the controller 106 can also include an error detection module 178 configured to detect when a measurement error may have occurred. The error detection module 178 can compare the photo detector output corresponding to the first receiver fiber 122R1 to the photo detector output corresponding to the second receiver fiber 122R2 (e.g., as described above with respect to FIGS. 8A and 8B), to determine the order in which the first and second receiver fibers encounter a marking or border crossing on the reference pattern 118. If the error detection module 178 detects that this order changes during a measurement (e.g., between the time when a start instruction and an end instruction are issued), the error detection module can flag that an error has occurred. For example, the error detection module 178 can cause an error LED to be illuminated, an audible alert to be sounded, and/or a visible message to be shown on the display 160. In some embodiments, the error detection module 178 can be configured to compensate for directional changes by decrementing the indicia count when it is detected that the user is moving the optical fibers 122 backwards along the reference pattern 118.

The controller 106 can also include an inflation control module 180 configured to actuate the inflation system 164. When an "inflate" instruction is issued (e.g., when the user pushes an inflate button or a start measurement button on the controller housing or on a touch screen display), the inflation control module 180 can cause power to be supplied to an electromechanical pump to begin pumping an inflation medium into the closed volume 116, or cause an electronically-actuated valve to open such that inflation media stored under pressure is placed in fluid communication with the closed volume via the inflation tube 124. In some embodiments, the inflation control module 180 can be configured to cut off power to the pump or to close a valve when a pressure sensor indicates that the pressure in the system has reached a predetermined threshold amount, thereby preventing over-inflation of the membrane.

The controller 106 can also include a display module 182 configured to display various information to the user on the display 160, such as menus, buttons, instructions, and other user interface elements. The display module 162 can also be configured to display instructions, warnings, errors, measurements, and calculations. For example, the display module 182 can be configured to display the palpable surface width ($PS_W$) and volume (V) of a prostate after a measurement procedure is completed on the prostate.

The controller 106 can also include an identification module 184 configured to determine whether the measurement assembly 104 is an authenticated measurement assembly. In some embodiments, the measurement assembly 104 can include an RFID tag, micro bar code, or other embedded identification information. The identification module 184 can be configured to read this identification information and compare it to a database of measurement assemblies. The database can be stored in the controller 106 or can be accessible via a network, and can indicate whether or not a particular measurement assembly 104 is authenticated. If the measurement assembly 104 is determined not to be authenticated, the identification module 184 can indicate as much to the user and can prevent the measurement from proceeding. If the measurement assembly 104 is determined to be authenticated, the identification module 184 can permit the measurement to proceed. When a measurement session is completed, the identification module 184 can be configured to create or mark an entry in the database indicating that the measurement assembly 104 used during the session is no longer authenticated, thereby preventing the measurement assembly 104 from being reused.

Connector System

As noted above, the system 100 can include one or more multiplex connector systems for coupling the measurement assembly 104 to the controller 106. FIGS. 11A-11H illustrate an exemplary embodiment of a connector system 200 in which a first fluid lumen and a first set of optical fibers (which can be disposed in the controller 106) can be selectively coupled to a second fluid lumen and a second set of optical fibers (which can be disposed in the measurement assembly 104). The illustrated connector system 200 can advantageously ensure proper alignment between the inflation and optical systems of the controller 106 and the measurement assembly 104. The connector system 200 can also allow the optical fibers to transition from a position outside of the inflation lumen to a position within the inflation lumen. The connector system 200 can include a first connector assembly 202A, a second connector assembly 202B, and a connector housing 204.

Figure 11B:
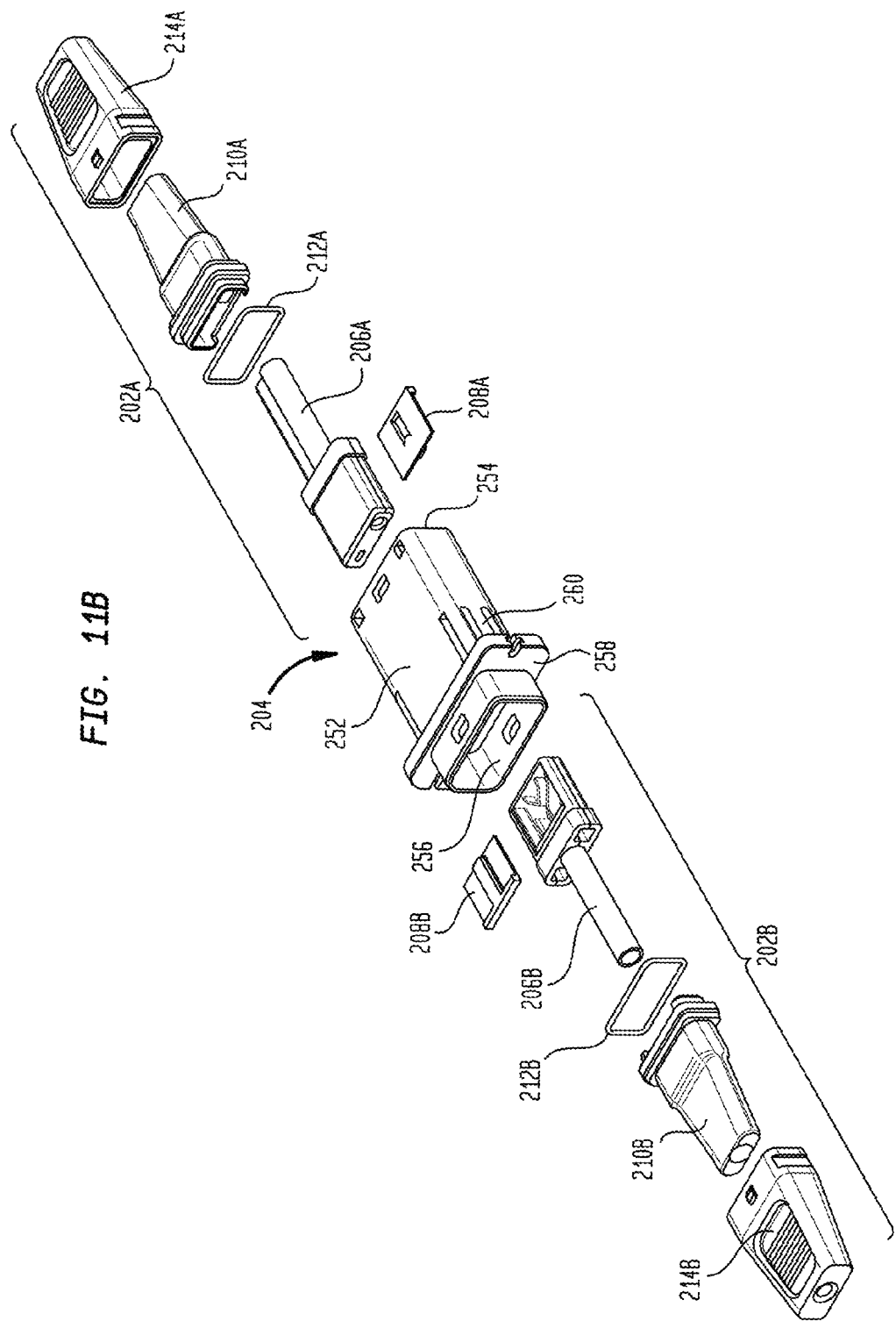
FIG. 11B is an exploded perspective view of a connector system.

As shown in FIG. 11B, the first connector assembly 202A can include a first connector body 206A, a first key plate 208A, a first internal overmold 210A, a first gasket 212A, and a first external overmold 214A.

As shown in FIG. 11C, the first connector body 206A can include a proximal extension portion 216A and a distal rectangular parallelepiped frame 218A. The proximal extension portion 216A can include a fluid passageway 220A and one or more fiber passageways 222A extending therethrough. The distal-facing surface of the frame 218A can define a first mating interface 224A configured to abut with a second mating interface 224B of the second connector body 206B, as discussed below. The frame 218A can also include internal baffles 226A that define a substantially H-shaped lumen 228A. In other words, the H-shaped lumen 228A can include first and second pathways that extend generally in the same direction with a crossover pathway joining the two together. As shown, a first leg 228A1 of the H-shaped lumen extends proximally to the fluid passageway 220A in the proximal extension portion 216A. A second leg 228A2 of the H-shaped lumen extends proximally to the fiber passageway(s) 222A in the proximal extension portion 216A. A third leg 228A3 of the H-shaped lumen extends distally to a fluid opening 230A formed in the first mating interface 224A. A fourth leg 228A4 of the H-shaped lumen extends distally to one or more fiber openings 232A formed in the first mating interface 224A.

Figure 11D:
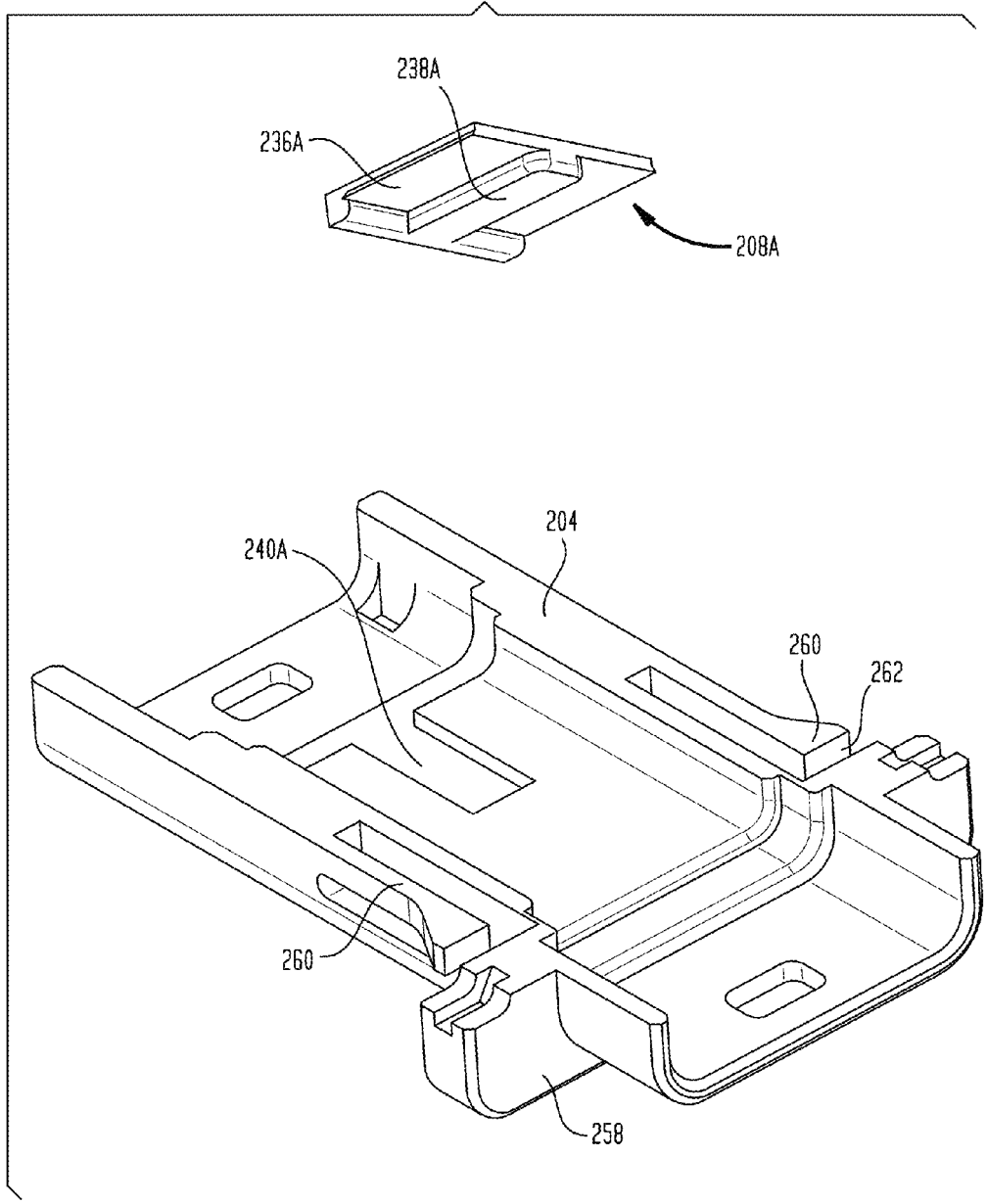
FIG. 11D is a perspective view of a first key plate and a connector housing.

The distal frame 218A can include at least one open face 234A through which the interior of the frame can be accessed. When assembled, the first key plate 208A can be glued to the frame 218A using an adhesive such that the first key plate covers the open face 234A of the frame. As shown in FIG. 11D, the first key plate 208A can include a planar base portion 236A with a raised key projection 238A configured to interface with a corresponding recess 240A in the connector housing 204. The size and shape of the projection 238A can be selected such that the first connector assembly 202A can only mate with the connector housing 204 in one orientation.

As shown in FIG. 11E, the first internal overmold 210A can be configured to slide over the proximal extension portion 216A and cover the proximal-facing surface of the distal frame 218A, or can be injection molded therearound. The first internal overmold 210A can be configured to support the proximal extension 216A and provide strain relief. The first internal overmold 210A can also include a lip 242A for forming the distal sidewall of a trough in which the first gasket 212A is seated.

The first gasket 212A can be configured to form a fluid-tight seal at the interface between the first connector assembly 202A and the connector housing 204. In some embodiments, the first gasket 212A can be a rubber O-ring.

The first external overmold 214A can be configured to slide over the first internal overmold 210A, or can be injection molded therearound, and can include a lip 244A for forming the proximal sidewall of the trough in which the first gasket 212A is seated. The first external overmold 214A can include a gripping surface 246A defined by a series of grooves or ribs, and can include raised tabs 248A and/or slots 250A configured to mate with corresponding features formed in the connector housing 204, such that the first connector assembly 202A can snap-fit into the connector housing 204.

Referring again to FIG. 11B, the second connector assembly 202B can include a second connector body 206B, a second key plate 208B, a second internal overmold 210B, a second gasket 212B, and a second external overmold 214B.

As shown in FIG. 11F, the second connector body 206B can include a distal extension portion 216B and a proximal rectangular parallelepiped frame 218B. The distal extension portion 216B can include a fluid passageway 220B extending therethrough. The proximal-facing surface of the frame 218B can define a second mating interface 224B configured to abut with the first mating interface 224A of the first connector body 206A, as discussed below. The frame 218B can also include internal baffles 226B that define a substantially H-shaped lumen 228B. In other words, the H-shaped lumen 228B can include first and second pathways that extend generally in the same direction with a crossover pathway joining the two together. As shown, a first leg 228B1 of the H-shaped lumen 228B extends distally to the fluid passageway 220B in the distal extension portion 216B. A second leg 228B2 of the H-shaped lumen 228B extends distally to a closed-off termination 252B formed by the wall of the frame 218B. A third leg 228B3 of the H-shaped lumen 228B extends proximally to a fluid opening 230B formed in the second mating interface 224B. A fourth leg 228B4 of the H-shaped lumen 228B extends proximally to one or more fiber openings 232B formed in the second mating interface 224B.

Figure 11G:
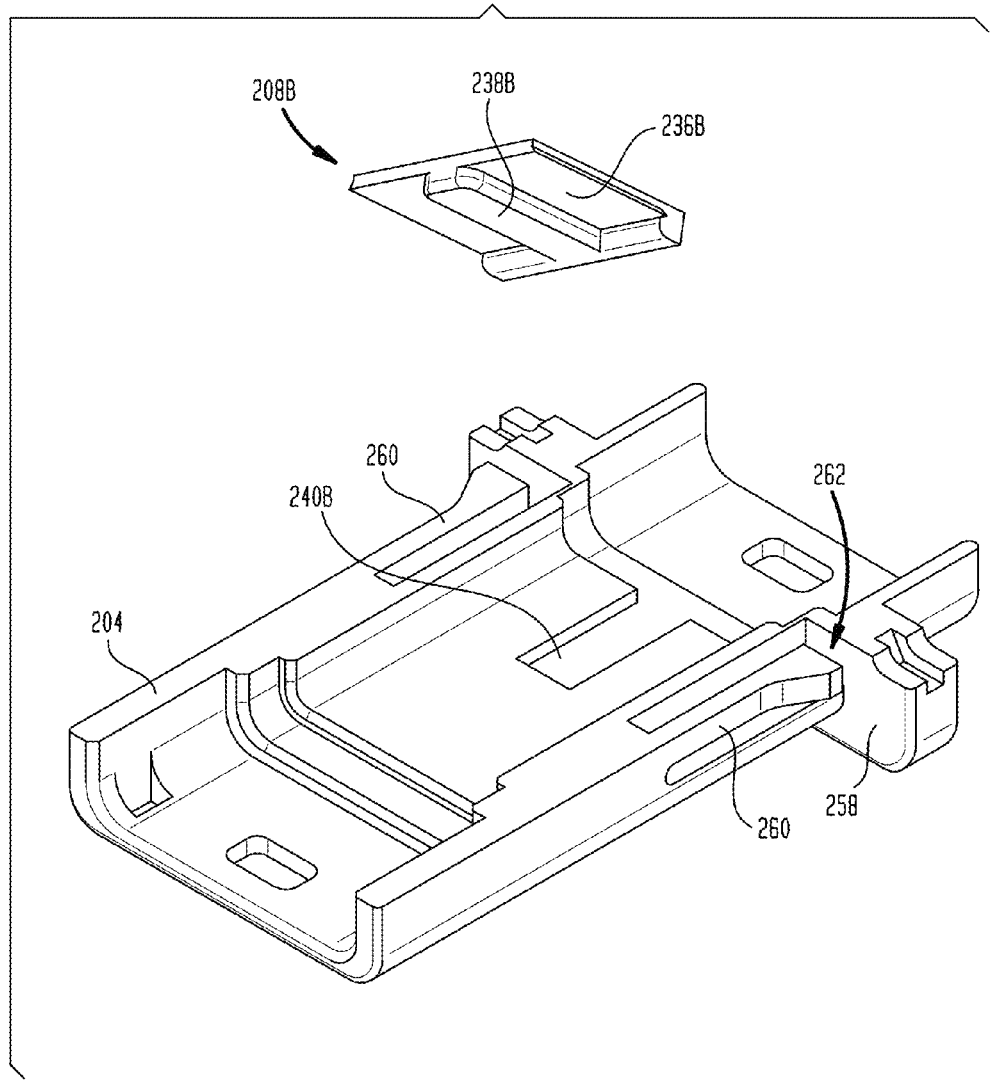
FIG. 11G is a perspective view of a second key plate and a connector housing.

The proximal frame 218B can include at least one open face 234B through which the interior of the frame can be accessed. When assembled, the second key plate 208B can be glued to the frame 218B using an adhesive such that the second key plate covers the open face 234B of the frame. As shown in FIG. 11G, the second key plate 208B can include a planar base portion 236B with a raised key projection 238B configured to interface with a corresponding recess 240B in the connector housing 204. The size and shape of the projection 238B can be selected such that the second connector assembly 202B can only mate with the connector housing 204 in one orientation. The second key plate 208B, which can form part of a disposable portion of the system 100, can include an RFID tag or other identifier which can be read by the identification module 184 as discussed above. In particular, the second key plate 208B can be injection molded around an RFID tag. It will be appreciated that the RFID tag can also be placed in any of a variety of other places in the disposable portion of the system 100, such as in the glove 110, the membrane 112, or the disposable portion's packaging.

Referring again to FIG. 11E, the second internal overmold 210B can be configured to slide over the distal extension portion 216B and cover the distal-facing surface of the proximal frame 218B, or can be injection molded therearound. The second internal overmold 210B can be configured to support the distal extension 216B and provide strain relief. The second internal overmold 210B can include a lip 242B for forming the proximal sidewall of a trough in which the second gasket 212B is seated.

The second gasket 212B can be configured to form a fluid-tight seal at the interface between the second connector assembly 202B and the connector housing 204. In some embodiments, the second gasket 212B can be a rubber O-ring.

The second external overmold 214B can be configured to slide over the second internal overmold 210B, or can be injection molded therearound, and can include a lip 244B for forming the distal sidewall of the trough in which the second gasket 212B is seated. The second external overmold 214B can include a gripping surface 246B defined by a series of grooves or ribs, and can include raised tabs 248B and/or slots 250B configured to mate with corresponding features formed in the connector housing 204, such that the second connector assembly 202B can snap-fit into the connector housing 204.

As shown in FIG. 11B, the connector housing can include a rectangular parallelepiped frame 252 with a proximal opening 254 for receiving the first connector assembly 202A and a distal opening 256 for receiving the second connector assembly 202B. The housing 204 can include key slots 240A, 240B for receiving the first and second key plates 208A, 208B, respectively, as shown in FIGS. 11D and 11G. The housing 204 can also include a mating flange 258 and spring arms 260 that together define a channel 262 in which the chassis of the controller 106 can be received. In particular, as the connector housing 204 is inserted through an opening in the controller chassis 264 during system assembly, the chassis wall 266 causes the spring arms 260 to deflect inwardly towards the housing 204. As the housing 204 is advanced further through the opening, the spring arms 260 surpass the chassis wall 266 and return outwardly away from the housing 204 to lock the chassis wall 266 in the channel 262, between the spring arms 260 and the flange 258, as shown for example in FIG. 12A. It will be appreciated that other techniques can also be used to mount, attach, or integrate the connector system 200 with the controller chassis 264. For example, the flange 258 can be configured to be disposed in the interior of the chassis 264, and/or can include one or more mounting screws or bolts for securing the housing 204 to the chassis 264. In some embodiments, the connector housing 204 can be formed integrally with at least one of the first connector body 206A and the second connector body 206B.

The components of the connector system 200 can be formed using a variety of techniques (e.g., stereolithography or injection molding) and from a variety of materials (e.g., polyvinyl chloride or polymethyl methacrylate (PMMA)).

Figure 11H:
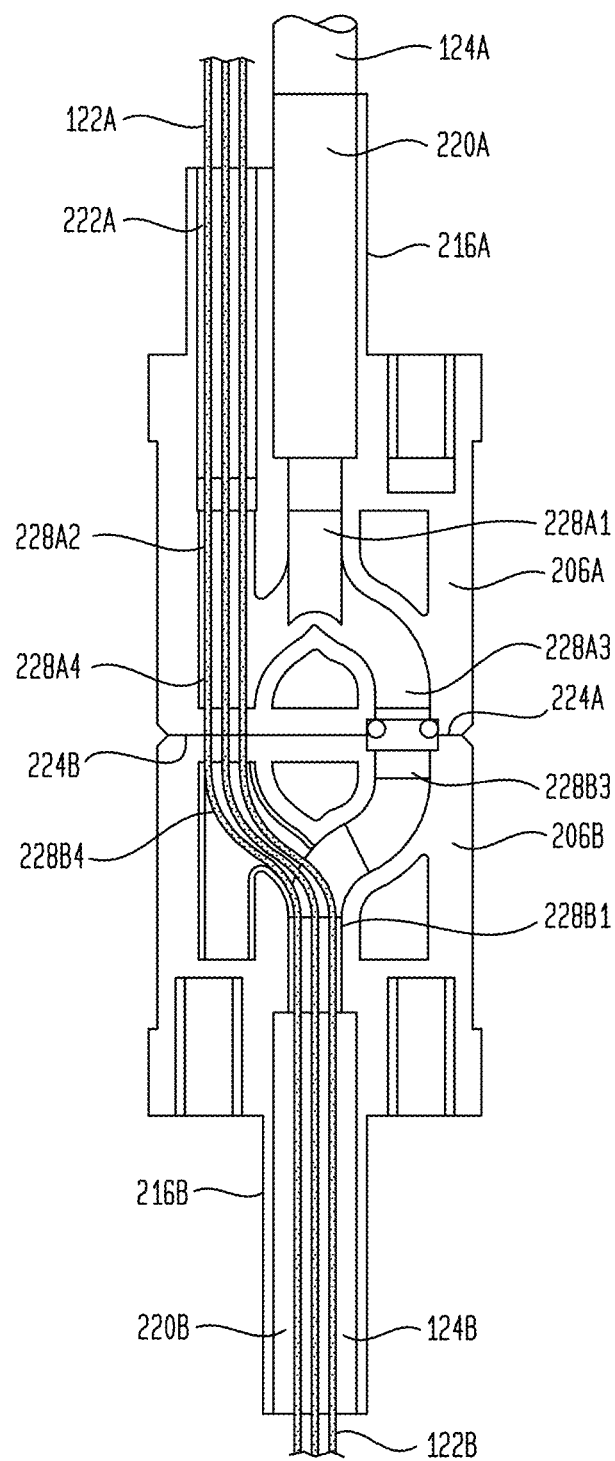
FIG. 11H is a cross-sectional top view of a connector system.

As shown in FIG. 11H, the first mating interface 224A of the first connector body 206A and the second mating interface 224B of the second connector body 206B can be placed in apposition such that fibers 122A extending through the first connector body are placed in optical communication with fibers 122B extending through the second connector body, and such that a fluid lumen 124A extending through the first connector body is placed in fluid communication with a fluid lumen 124B extending through the second connector body. The first mating interface 224A can be maintained in alignment with the second mating interface 224B by the connector housing 204.

Figure 12A:
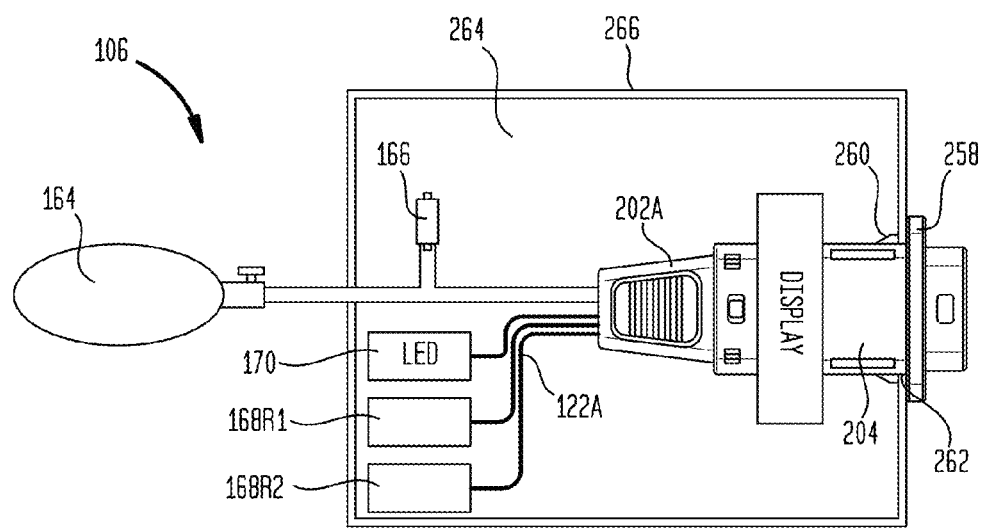
FIG. 12A is a schematic view of a reusable portion of an examination system.

As also shown in FIG. 11H, the connector system 200 can allow one or more optical fibers 122 to be introduced into a fluid-tight passage (e.g., the inflation tube 124 of a prostate evaluation system 100). In the illustrated connector system 200, a first set of three optical fibers 122A enters the proximal end of the first connector body 206A through the fiber passageway 222A in the proximal extension portion 216A. The fibers 122A then extend through the second leg 228A2 of the H-shaped lumen and into the fourth leg 228A4, where their terminal distal ends are presented at the first mating interface 224A. The terminal proximal ends of the fibers 122A can be coupled to the light source 170 and optical sensors 168R1, 168R2 of the controller 106, as shown in FIG. 12A. The first set of optical fibers 122A can thus extend through less than an entire length of the fluid lumen formed in the first connector body 206A.

Figure 12B:
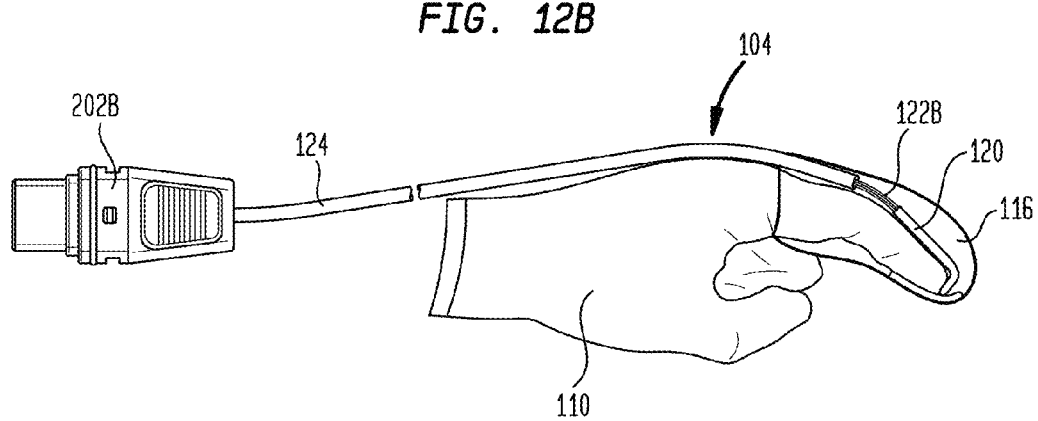
FIG. 12B is a schematic view of a disposable portion of an examination system.

A second set of three optical fibers 122B enters the distal end of the second connector body 206B through the inflation lumen 220B in the distal extension portion 216B. The fibers 122B then extend through the first leg 228B1 of the H-shaped lumen, through the crossover path, and into the fourth leg 228B4, where their terminal proximal ends are presented at the second mating interface 224B. The terminal distal ends of the fibers 122B can be mounted in the finger clip 120, as shown in FIG. 12B.

In some embodiments, the ends of the fibers 122A, 122B presented at the first and second mating interfaces 224A, 224B can be square-cut to form a butt joint with each other. In other embodiments, the ends of the fibers 122A, 122B can be slash- or oblique-cut to form a miter joint with each other. Use of a miter joint can, in some instances, reduce reflections produced at the fiber junction, and thereby reduce noise and improve measurement accuracy.

In addition to providing a fiber path, the connector system 200 can define a fluid-tight passageway extending therethrough. Fluid supplied from the controller inflation system (e.g., from a manual pump 164 and pressure relief valve 166 as shown in FIG. 12A) can enter the proximal end of the fluid passageway 220A and can flow through the first and third legs 228A1, 228A3 of the H-shaped lumen in the first connector body 206A. The fluid can then flow across the intersection of the first and second mating interfaces 224A, 224B, and into the third and first legs 228B3, 228B1 of the H-shaped lumen in the second connector body 206B. The fluid can then flow through the fluid passageway 220B formed in the distal extension portion 216B (e.g., to the inflation tube 124 leading to the sealed membrane volume 116 of the measurement assembly 104, as shown in FIG. 12B).

The mated connector system 200 thus provides a continuous fluid-tight passage having proximal and distal terminal ends, in which one or more optical fibers 122 can enter the fluid-tight passage at a location other than the proximal and distal terminal ends. In other words, the connector system 200 can allow optical fibers 122 to extend from a position outside of the inflation path to a position inside the inflation path without losing inflation pressure.

It will be appreciated that the system 100 can be divided into a reusable portion and a disposable portion. The reusable portion, shown in FIG. 12A, can include the controller 106, the connector housing 204 mounted in the controller chassis 264, and the first connector assembly 202A disposed within the controller chassis. The disposable portion, shown in FIG. 12B, can include the second connector assembly 202B and the measurement assembly 104. The connector system 200 can thus allow for quick and easy connection/disconnection of the optical and fluid systems of the reusable portion and the disposable portion in a single operation.

Methods

An exemplary method of using the system 100 to measure a patient's prostate is as follows. First, the user can remove the disposable portion of the system (e.g., the measurement assembly 104 and the second connector assembly 202B) from its packaging. The user can then couple the disposable portion to the reusable portion of the system. For example, the second connector assembly 202B can be inserted into the connector housing 204 mounted in the controller 106. The user can then don the glove 110 and insert their forefinger into the patient's rectum. As noted above, the finger clip 120 can be attached to the dorsal and distal surfaces of the user's finger, such that the ventral surface of the user's finger remains free to perform a digital rectal examination as would conventionally be done with a standard exam glove. The user can therefore perform a standard digital rectal examination and obtain a prostate measurement using the system 100 without changing gloves.

When the user is ready to take a measurement, the membrane 112 can be positioned adjacent to the rectal wall in proximity to the prostate 102. The membrane 112 can then be inflated such that the membrane expands into contact with the rectal wall. The membrane 112 can be inflated by actuating a manual pump, or by pushing a button or other user interface element on the controller 106 to activate an electromechanical pump, valve, or other inflation system component. As explained above, when the membrane 112 is inflated, the spacing 128 and width of the indicia 126 on the reference pattern 118 can remain substantially constant.

Before or after inflating the membrane 112, the user can locate a first prostate lateral margin with their finger. The user can then push a button or other user interface element on the controller 106 to initiate execution of a measurement routine by the processor 152. The button or user interface element for initiating a measurement can be the same as the one for inflating the membrane 112, such that a single button push is effective to both inflate the membrane and initiate a measurement. Separate buttons can alternatively be provided. The user can then swipe their finger from the first prostate lateral margin to the second prostate lateral margin, thereby moving the finger clip 120 and associated optical fibers 122 along the measurement axis M of the reference pattern 118, as the reference pattern and membrane 112 remain stationary against the rectal wall.

As the user's finger moves across the reference pattern 118, light generated by the light source 170 can be transmitted to the reference pattern through the transmitting fiber 122T, and reflected back from the reference pattern to the optical detectors 168R1, 168R2 through the first and second receiver fibers 122R1, 122R2. As the receiver fibers move from a light region 128 to a dark region 126 and vice-versa, the optical sensor outputs provided to the processor 152 change. The processor 152 can maintain a count of such transitions until the user reaches the second prostate lateral margin, at which time the user can end the measurement procedure, for example by pushing a button or user interface element on the controller 106, or by holding their finger stationary such that a predetermined time elapses without a change in sensor output, thereby triggering the processor to end the measurement routine. If the user changes the direction in which they are moving their finger during the measurement routine, such a change in direction can be detected as described above and can trigger an error message to the user or compensation processing.

When the measurement procedure is finished, the processor 152 can calculate or estimate values for the palpable surface width and/or volume of the prostate as described above. These values can then be displayed on the display 160, stored in the storage device 158, and/or transmitted to the computer system 108 for storage and/or further processing. For example, the measured volume of the prostate can be compared to a threshold volume based on the patient's age or other factors to determine whether a biopsy should be recommended to the patient. When the user is finished taking measurements, the membrane can be deflated (e.g., automatically upon the user's pressing of an "end measurement" button) and the measurement assembly 104 can be removed from the patient. The second connector assembly 202B can be unplugged from the connector housing 204 and the disposable portion of the system 100 can be taken off and discarded in accordance with proper medical waste disposal procedures. In some embodiments, the "disposable" portion of the system 100 can also be cleaned and/or sterilized for subsequent reuse.

While the systems and methods disclosed herein are generally described in connection with measuring a human prostate for diagnostic purposes, it will be appreciated that many other applications exist for such systems and methods. For example, the systems and methods disclosed herein can be used to measure any object, including any portion of a human or animal body. In addition, the systems and methods disclosed herein can be used to measure colorectal cancers or lesions that are within a finger's length into the rectum or to check for benign prostatic hyperplasia.

As used herein, the term "fluid" refers to both liquids (e.g., water or saline) and gasses (e.g., air, nitrogen, or carbon dioxide).

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A system for estimating the volume of a prostate, comprising:
   a transmitting fiber;
   a light source that produces light to be transmitted through the transmitting fiber;
   first and second receiver fibers;
   a first detector circuit that receives light transmitted through the first receiver fiber after being transmitted through the transmitting fiber and reflected back from a reference pattern of a measurement assembly;
   a second detector circuit that receives light transmitted through the second receiver fiber after being transmitted through the transmitting fiber and reflected back from the reference pattern of the measurement assembly;
   a processor programmed to provide:
   a sensor input module configured to receive a first signal from the first detector circuit indicative of light reflected from the reference pattern through the first receiver fiber and a second signal from the second detector circuit indicative of light reflected from the reference pattern through the second receiver fiber as at least a portion of the measurement assembly is moved across the reference pattern from a first prostate lateral margin to a second prostate lateral margin, the sensor module being configured to detect based on a timing at which light reflected from the reference pattern is detected through the first and second receiver fibers when a change in the direction in which the portion of the measurement assembly moves relative to the reference pattern occurs,
   a distance measuring module configured to convert the first and second signals into a measured prostate palpable surface width ($PS_W$),
   a volume estimation module configured to estimate a volume (V) of the prostate based on the measured palpable surface width ($PS_W$), and
   an error detection module configured to detect that a measurement error has occurred when the sensor module detects that the direction of movement changed and, in response to the error, at least one of (i) adjust the measured palpable surface width ($PS_W$) to compensate for the change in direction and (ii) alert a user that a change in direction occurred.

2. The system of claim 1, wherein the volume estimation module estimates the volume (V) as $V=PS_W^3 \times k$, wherein k is a constant.

3. The system of claim 2, wherein k is between 0.35 and 0.45.

4. The system of claim 2, wherein k is 0.3926991.

5. The system of claim 1, wherein the processor is programmed to provide a display module configured to drive a display to display the estimated volume (V).

6. The system of claim 1, wherein the processor is programmed to provide an inflation control module configured to actuate a pump or a control valve to inflate a membrane disposed around a digit extension of a glove to a predetermined pressure or with a predetermined volume of air.

7. The system of claim 1, wherein the processor is programmed to provide an RFID interface module configured to receive information indicative of an RFID signature of a disposable unit and to determine whether the disposable unit is an authenticated disposable unit.

8. A method of estimating the volume of a prostate, comprising:
   moving a transmitting optical fiber, a first receiving optical fiber, and a second receiving optical fiber across a reference pattern from a first lateral margin of a prostate to a second lateral margin of the prostate to generate information indicative of light reflected from the reference pattern;
   using at least one processor to determine from the generated information when a change in direction of movement across the reference pattern occurs based on the timing at which light reflected from the reference pattern is detected through the first and second receiving optical fibers;
   using at least one processor to convert the generated information into a measured prostate palpable surface width ($PS_W$);
   using the at least one processor to estimate a volume (V) of the prostate based on the measured palpable surface width ($PS_W$); and
   when a change in the direction of movement occurs, at least one of (i) adjusting the measured palpable surface width ($PS_W$) to compensate for the change in direction and (ii) alerting a user that a change in direction occurred.

9. The method of claim 8, further comprising estimating the volume (V) as $V=PS_W^3 \times k$, wherein k is a constant.

10. The method of claim 9, wherein k is between 0.35 and 0.45.

11. The method of claim 9, wherein k is 0.3926991.

12. The method of claim 8, further comprising using the at least one processor to drive a display to display the estimated volume (V).

13. The method of claim 8, further comprising using the at least one processor to actuate a pump or a control valve to inflate a membrane disposed around a digit extension of a glove to a predetermined pressure or with a predetermined volume of air.

14. The method of claim 8, further comprising using the at least one processor to receive information indicative of an RFID signature of a disposable unit and to determine whether the disposable unit is an authenticated disposable unit.

* * * * *